US012657939B1

(12) United States Patent
Fay et al.

(10) Patent No.: US 12,657,939 B1
(45) Date of Patent: Jun. 16, 2026

(54) UTILIZING MACHINE LEARNING MODELS TO SYNTHESIZE PERTURBATION DATA TO GENERATE PERTURBATION HEATMAP GRAPHICAL USER INTERFACES

(71) Applicant: Recursion Pharmaceuticals, Inc., Salt Lake City, UT (US)

(72) Inventors: Marta Marie Fay, Salt Lake City, UT (US); August Orvis Allen, Boulder, CO (US); Eugene Yin-Chung Ting, Toronto (CA); Lina Maria Nilsson, Salt Lake City, UT (US); Condie Thomas Swallow, II, West Valley City, UT (US); Michael Haines, Salt Lake City, UT (US); Denton Hallar Greenfield, Evansville, IN (US); Kristin Ann Clark, Lehi, UT (US); Lovina Roundy, Orem, UT (US); Michael Joseph Uloth, Dundas (CA); Sara Marjean Moore, Boise, ID (US); Shweta Deepchand Bhandare, Boulder, CO (US); Ted Douglas Monchamp, Nashua, NH (US); Summer Walid Elias, Salt Lake City, UT (US); Berton Allen Earnshaw, Cedar Hills, UT (US); Mason Lemoyne Victors, Riverton, UT (US); Safiye Celik, Sudbury, MA (US); James Benjamin Taylor, Midlothian, VA (US); Andrew David Blevins, Salt Lake City, UT (US); James Douglas Jensen, Farmington, UT (US); Jacob Carter Cooper, Sandy, UT (US); Conor Austin Forsman Tillinghast, Salt Lake City, UT (US); Seyhmus Guler, Salt Lake City, UT (US); Kyle Rollins Hansen, Kaysville, UT (US); Sarah Jordan DeVore, Salt Lake City, UT (US); Tongzhou Shen, Surrey (CA)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 332 days.

(21) Appl. No.: 18/526,707

(22) Filed: Dec. 1, 2023

Related U.S. Application Data

(60) Provisional application No. 63/582,702, filed on Sep. 14, 2023.

(51) Int. Cl.
*G16B 15/00* (2019.01)
*G06V 10/74* (2022.01)
(Continued)

(52) U.S. Cl.
CPC .......... *G06V 20/698* (2022.01); *G06V 10/761* (2022.01); *G06V 10/82* (2022.01); *G16B 15/00* (2019.02)

(58) Field of Classification Search
CPC .... G06V 20/698; G06V 10/761; G06V 10/82; G16B 15/00
See application file for complete search history.

(56) References Cited

U.S. PATENT DOCUMENTS

| | | | |
|---|---|---|---|
| 7,047,410 B1 | 5/2006 | Shin | |
| 8,812,526 B2 | 8/2014 | Ramer et al. | |

(Continued)

OTHER PUBLICATIONS

Sivanandan, S., et al. "A pooled cell painting CRISPR screening platform enables de novo inference of gene function by self-supervised deep learning bioRxiv preprint 2023; bioRxiv Aug. 2023. 13.553051." (Year: 2023).*

(Continued)

*Primary Examiner* — Gregory A Morse
*Assistant Examiner* — Renae A Bitor
(74) *Attorney, Agent, or Firm* — Keller Preece PLLC

(57) ABSTRACT

The present disclosure relates to systems, non-transitory computer-readable media, and methods for embedding perturbation data via a machine learning model and filtering, aligning, and aggregating the embeddings to generate a genome-wide perturbation database for real-time generation (Continued)

of perturbation heatmaps. In particular, in one or more embodiments, the disclosed systems can receive a plurality of perturbation images portraying cells from a plurality of wells corresponding to a plurality of cell perturbations. Further, the systems can generate, utilizing a machine learning model, a plurality of well-level image embeddings from the plurality of perturbation images. Moreover, the systems can align, utilizing an alignment model, the plurality of well-level image embeddings to generate aligned well-level image embeddings. Additionally, the systems can aggregate, according to perturbations of one or more perturbation experiments, the well-level image embeddings to generate perturbation-level image embeddings. Furthermore, the systems can generate perturbation comparisons utilizing the perturbation-level image embeddings.

20 Claims, 16 Drawing Sheets

(51) Int. Cl.
  *G06V 10/82* (2022.01)
  *G06V 20/69* (2022.01)

(56) References Cited

U.S. PATENT DOCUMENTS

| | | | |
|---|---|---|---|
| 10,146,914 | B1 | 12/2018 | Victors et al. |
| 10,769,501 | B1 * | 9/2020 | Ando ............... G01N 33/5005 |
| 12,073,638 | B1 | 8/2024 | Lazar et al. |
| 12,079,992 | B1 | 9/2024 | Lazar et al. |
| 12,119,090 | B1 | 10/2024 | Kraus et al. |
| 12,373,950 | B1 | 7/2025 | Minasian et al. |
| 12,374,429 | B1 | 7/2025 | Fay et al. |
| 2010/0223276 | A1 | 9/2010 | Al-Shameri et al. |
| 2015/0320319 | A1 | 11/2015 | Alfano et al. |
| 2019/0114390 | A1 | 4/2019 | Donner et al. |
| 2020/0126637 | A1 * | 4/2020 | Xu .......................... G16B 20/00 |
| 2021/0133976 | A1 | 5/2021 | Carmi |
| 2021/0257044 | A1 | 8/2021 | Califano et al. |
| 2021/0366577 | A1 * | 11/2021 | Koller .................... G16B 40/20 |
| 2021/0374553 | A1 | 12/2021 | Li et al. |
| 2022/0180975 | A1 | 6/2022 | Regev et al. |
| 2023/0416307 | A1 | 12/2023 | Lopez et al. |
| 2024/0112447 | A1 | 4/2024 | Sawada et al. |
| 2024/0304009 | A1 | 9/2024 | Yoon et al. |
| 2026/0051164 | A1 | 2/2026 | Nykl et al. |

OTHER PUBLICATIONS

U.S. Appl. No. 18/526,729, May 27, 2025, Notice of Allowance.

Akshay Agrawal, Alnur Ali, Stephen Boyd, et al. Minimum-distortion embedding. Foundations and Trends® in Machine Learning, 14(3):211-378, 2021.

Arthur Liberzon, Chet Birger, Helga Thorvaldsdóttir, Mahmoud Ghandi, Jill P Mesirov, and Pablo Tamayo. The molecular signatures database hallmark gene set collection. Cell systems, 1(6):417-425, 2015.

Atray Dixit, Oren Parnas, Biyu Li, Jenny Chen, Charles P Fulco, Livnat Jerby-Arnon, Nemanja D Marjanovic, Danielle Dionne, Tyler Burks, Raktima Raychowdhury, et al. Perturb-seq: dissecting molecular circuits with scalable single-cell rna profiling of pooled genetic screens. cell, 167(7):1853-1866, 2016.

Aurora S Blucher, Safiye Celik, James D Jensen, James Taylor, Michael F Cuccarese, Jacob C Cooper, Jacob M Rinaldi, Carl Brooks, Michael A Statnick, Marta Fay, Nathan Lazar, Berton Earnshaw, and Imran S Haque. Poster: Mapping biology with a unified representation space for genomic and chemical perturbations to enable accelerated drug discovery. In Learning Meaningful Representation of Life Workshop at NeurIPS, 2021.

D Michael Ando, Cory Y McLean, and Marc Berndl. Improving phenotypic measurements in high-content imaging screens. BioRxiv, p. 161422, 2017.

Gabor J Szekely. Potential and kinetic energy in statistics. Lecture Notes, Budapest Institute, 1989.

Gökcen Eraslan, Lukas M Simon, Maria Mircea, Nikola S Mueller, and Fabian J Theis. Singlecell rna-seq denoising using a deep count autoencoder. Nature communications, 10(1):1-14, 2019.

John W Tukey. Mathematics and the picturing of data. In Proceedings of the International Congress of Mathematicians, Vancouver, 1975, vol. 2, pp. 523-531, 1975.

Joseph M Replogle, Reuben A Saunders, Angela N Pogson, Jeffrey A Hussmann, Alexander Lenail, Alina Guna, Lauren Mascibroda, Eric J Wagner, Karen Adelman, Gila Lithwick-Yanai, et al. Mapping information-rich genotype-phenotype landscapes with genome-scale perturb-seq. Cell, 2022.

Kevin Drew, John B Wallingford, and Edward M Marcotte. hu.map 2.0: integration of over 15,000 proteomic experiments builds a global compendium of human multiprotein assemblies. Mol Syst Biol, 17(5):e10016, 2021.

Kihyuk Sohn, Honglak Lee, and Xinchen Yan. Learning structured output representation using deep conditional generative models. Advances in neural information processing systems, 28, 2015.

Krzysztof Polanski, Matthew D Young, Zhichao Miao, Kerstin B Meyer, Sarah A Teichmann, and Jong-Eun Park. Bbknn: fast batch alignment of single cell transcriptomes. Bioinformatics, 36(3):964-965, 2020.

Laleh Haghverdi, Aaron TL Lun, Michael D Morgan, and John C Marioni. Batch effects in single-cell rna-sequencing data are corrected by matching mutual nearest neighbors. Nature biotechnology, 36(5):421-427, 2018.

Leland McInnes, John Healy, and James Melville. Umap: Uniform manifold approximation and projection for dimension reduction. arXiv preprint arXiv:1802.03426, 2018.

Luana Licata, Prisca Lo Surdo, Marta Iannuccelli, Alessandro Palma, Elisa Micarelli, Livia Perfetto, Daniele Peluso, Alberto Calderone, Luisa Castagnoli, and Gianni Cesareni. Signor 2.0, the signaling network open resource 2.0: 2019 update. Nucleic acids research, 48(D1): D504-D510, 2020.

Madalina Giurgiu, Julian Reinhard, Barbara Brauner, Irmtraud Dunger-Kaltenbach, Gisela Fobo, Goar Frishman, Corinna Montrone, and Andreas Ruepp. Corum: the comprehensive resource of mammalian protein complexes—2019. Nucleic acids research, 47(D1):D559-D563, 2019.

Marc Gillespie, Bijay Jassal, Ralf Stephan, Marija Milacic, Karen Rothfels, Andrea Senff-Ribeiro, Johannes Griss, Cristoffer Sevilla, Lisa Matthews, Chuqiao Gong, et al. The reactome pathway knowledgebase 2022. Nucleic acids research, 50(D1):D687-D692, 2022.

Maria L Rizzo and Gábor J Székely. Energy distance. wiley interdisciplinary reviews: Computational statistics, 8(1):27-38, 2016.

Mark-Anthony Bray, Shantanu Singh, Han Han, Chadwick T Davis, Blake Borgeson, Cathy Hartland, Maria Kost-Alimova, Sigrun M Gustafsdottir, Christopher C Gibson, and Anne E Carpenter. Cell painting, a high-content image-based assay for morphological profiling using multiplexed fluorescent dyes. Nature protocols, 11(9):1757-1774, 2016.

Michael F Cuccarese, Berton A Earnshaw, Katie Heiser, Ben Fogelson, Chadwick T Davis, Peter F McLean, Hannah B Gordon, Kathleen-Rose Skelly, Fiona L Weathersby, Vlad Rodic, Ian K Quigley, Elissa D Pastuzyn, Brandon M Mendivil, Nathan H Lazar, Carl A Brooks, Joseph Carpenter, Brandon L Probst, Pamela Jacobson, Seth W Glazier, Jes Ford, James D Jensen, Nicholas D Campbell, Michael A Statnick, Adeline S Low, Kirk R Thomas, Anne E Carpenter, Sharath S Hegde, Ronald W Alfa, Mason L Victors, Imran S Haque, Yolanda T Chong, and Christopher C Gibson. Functional immune mapping with deep-learning enabled phenomics applied to immunomodulatory and covid-19 drug discovery. bioRxiv, 2020. doi: 10.1101/2020.08.02.233064.

Nathan Lazar, et al. High-Resolution Genome-wide Mapping of Chromosome-arm-scale Truncations Induced by CRISPR-Cas9 Editing published in bioRxiv on Apr. 15, 2023.

(56)           References Cited

OTHER PUBLICATIONS

Romain Lopez, Jeffrey Regier, Michael B Cole, Michael I Jordan, and Nir Yosef. Deep generative modeling for single-cell transcriptomics. Nature methods, 15(12):1053-1058, 2018.

U.S. Appl. No. 18/526,729, Jan. 16, 2025, Office Action.

U.S. Appl. No. 18/393,041, May 3, 2024, Notice of Allowance.

Sivanandan et al. "A Pooled Cell Painting CRISPR Screening Platform Enables de novo Inference of Gene Function by Self-supervised Deep Learning", https://www.biorxiv.org/contenU10.1101/2023.08.13.553051v3.abstract, bioRxiv 2023.08.13.553051; https://doi.org/10.1101/2023.08.13.553051; pp. 1-49; Aug. 27, 2023 (Year: 2023).

U.S. Appl. No. 18/392,989, Mar. 1, 2024, Office Action.

U.S. Appl. No. 18/392,989, Apr. 29, 2024, Notice of Allowance.

Yihan Zhang, Luing Yang, and Vladimir Brusic, "Automation of Gene Expression Profile Analysis in Single Cell Data", 2020 IEEE International Conference on Bioinformatics and Biomedicine (BIBM), Seoul, Korea (South), 2020, pp. 1329-1334, doi: 10.1109/BIBM49941.2020.9313510. (Year: 2020).

U.S. Appl. No. 18/526,742, Apr. 3, 2026, Notice of Allowance.

* cited by examiner

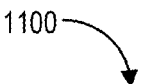

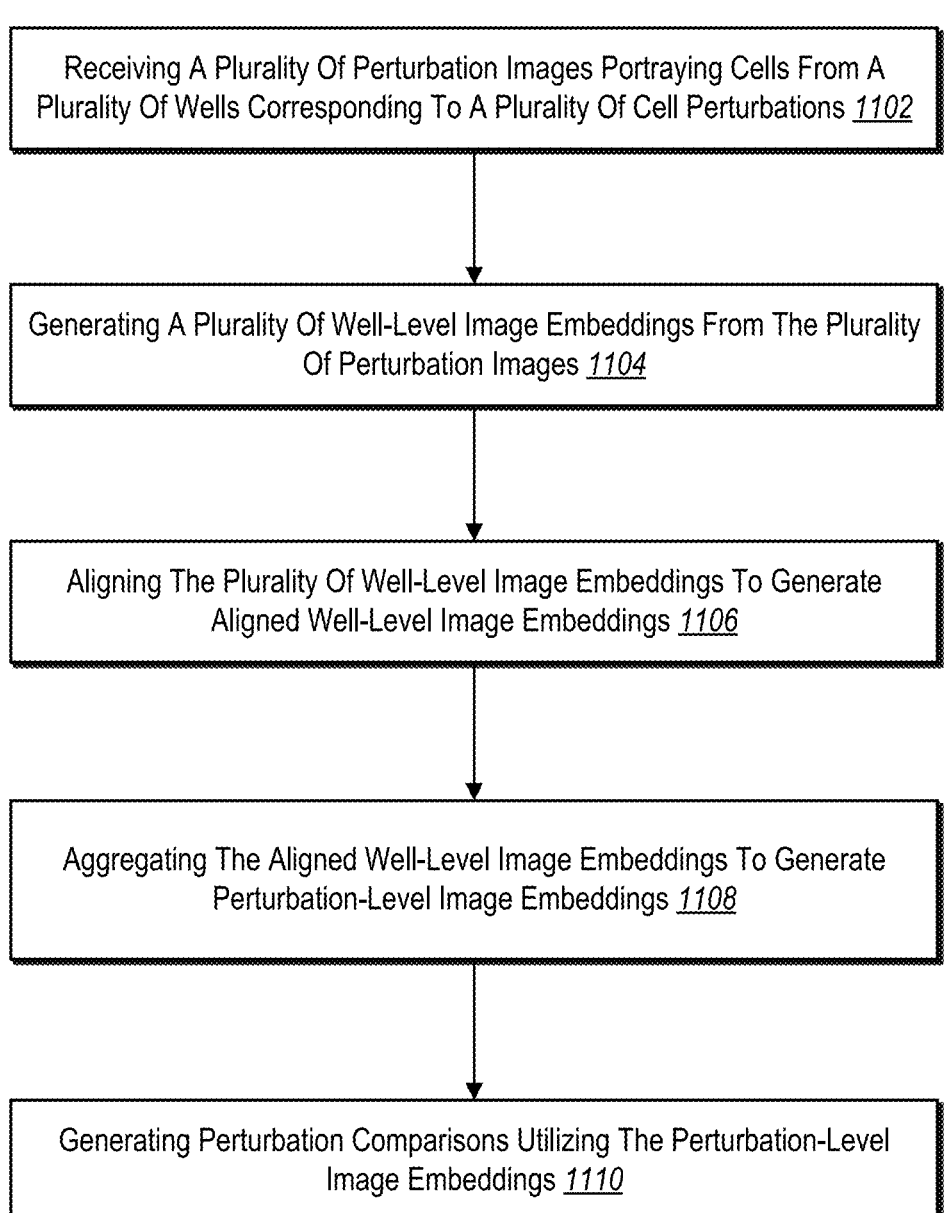

Receiving A Plurality Of Perturbation Images Portraying Cells From A Plurality Of Wells Corresponding To A Plurality Of Cell Perturbations *1102*

Generating A Plurality Of Well-Level Image Embeddings From The Plurality Of Perturbation Images *1104*

Aligning The Plurality Of Well-Level Image Embeddings To Generate Aligned Well-Level Image Embeddings *1106*

Aggregating The Aligned Well-Level Image Embeddings To Generate Perturbation-Level Image Embeddings *1108*

Generating Perturbation Comparisons Utilizing The Perturbation-Level Image Embeddings *1110*

*Fig. 11*

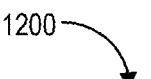

1200

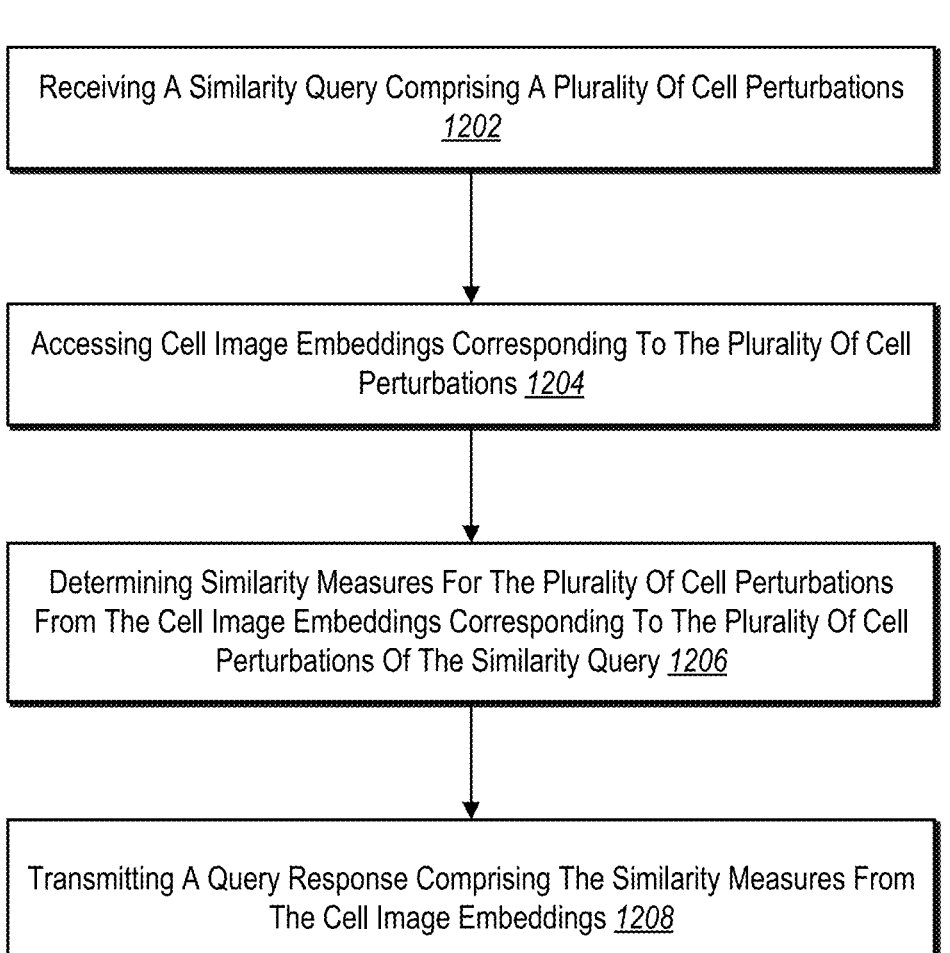

Receiving A Similarity Query Comprising A Plurality Of Cell Perturbations *1202*

Accessing Cell Image Embeddings Corresponding To The Plurality Of Cell Perturbations *1204*

Determining Similarity Measures For The Plurality Of Cell Perturbations From The Cell Image Embeddings Corresponding To The Plurality Of Cell Perturbations Of The Similarity Query *1206*

Transmitting A Query Response Comprising The Similarity Measures From The Cell Image Embeddings *1208*

*Fig. 12*

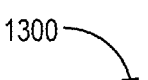

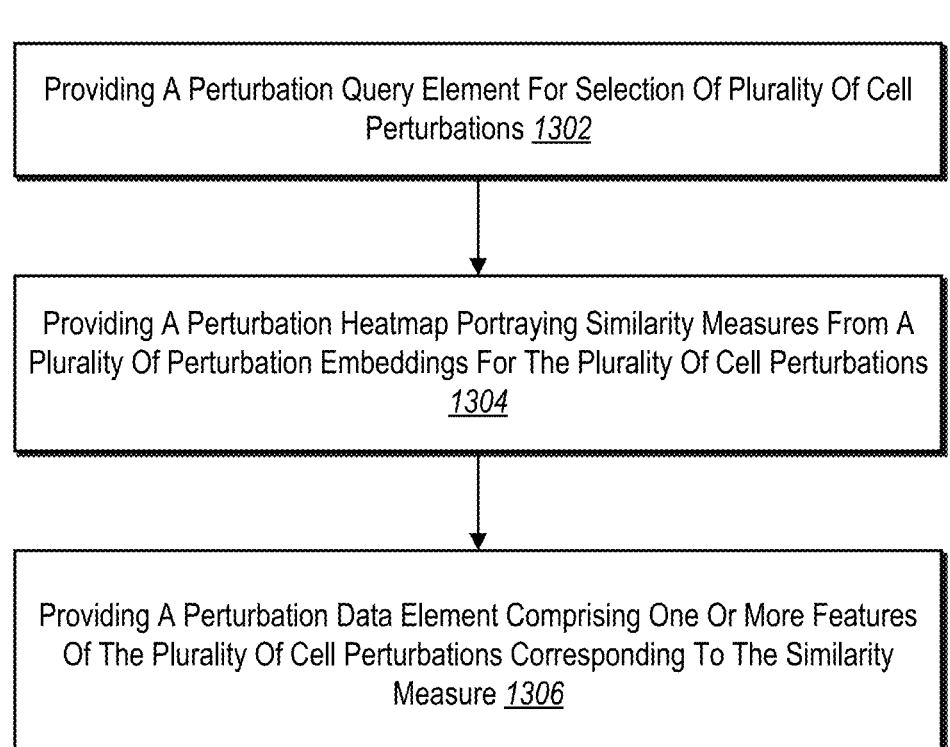

Providing A Perturbation Query Element For Selection Of Plurality Of Cell Perturbations *1302*

Providing A Perturbation Heatmap Portraying Similarity Measures From A Plurality Of Perturbation Embeddings For The Plurality Of Cell Perturbations *1304*

Providing A Perturbation Data Element Comprising One Or More Features Of The Plurality Of Cell Perturbations Corresponding To The Similarity Measure *1306*

*Fig. 13*

UTILIZING MACHINE LEARNING MODELS TO SYNTHESIZE PERTURBATION DATA TO GENERATE PERTURBATION HEATMAP GRAPHICAL USER INTERFACES

CROSS REFERENCE TO RELATED APPLICATIONS

This application claims the benefit of and priority to U.S. Provisional Application No. 63/582,702, filed Sep. 14, 2023. The aforementioned application is hereby incorporated by reference in its entirety.

BACKGROUND

Recent years have seen significant improvements in hardware and software platforms for utilizing computing devices to extract and analyze digital signals corresponding to biological relationships. For example, conventional systems can generate user interfaces for searching digital content reflecting digital information between particular genes, diseases, and/or treatments. To illustrate, conventional systems can search digital repositories for experimental data or digital articles and present query results for display (e.g., in the form of curated lists and/or pre-generated data tables). Client devices can utilize a variety of user interfaces to further analyze these digital results utilizing a brute-force approach. Although conventional systems can perform search analysis and generate a large volume of user interfaces for analyzing such data, conventional systems have a number of technical deficiencies with regard to inaccuracy, inefficiency, and operational inflexibility in utilizing large digital data volumes across computer networks to support discovery and display of biological relationships.

SUMMARY

Embodiments of the present disclosure provide benefits and/or solve one or more of the foregoing or other problems in the art with systems, non-transitory computer-readable media, and methods for embedding perturbation data via a machine learning model and filtering, aligning, and aggregating the embeddings to generate a genome-wide perturbation database for real-time generation of perturbation heatmaps. In particular, the disclosed systems can synthesize phenomic digital images representing cellular perturbations by embedding the phenomic digital images into a low dimensional space via a machine learning model. Moreover, in one or more embodiments, the disclosed systems apply various filtering, aligning, and aggregation models for compilation into a perturbation database. Indeed, by aligning the perturbation data across different experiments, the disclosed systems can accurately relate experimental data from any number of perturbation experiments into an accurate machine learning representation of the underlying biology. Further, the disclosed systems can identify perturbation relationships by accessing the database, in response to a query of one or more perturbations, and determine a similarity measure between the queried perturbations utilizing the genome wide perturbations in the database. Additionally, the disclosed systems can generate, for display on a client device, an interactive heatmap of the identified perturbation relationships along with additional user interface elements for efficient analysis of perturbation relationships.

Additional features and advantages of one or more embodiments of the present disclosure are outlined in the description which follows, and in part can be determined from the description, or may be learned by the practice of such example embodiments.

BRIEF DESCRIPTION OF THE DRAWINGS

The detailed description provides one or more embodiments with additional specificity and detail through the use of the accompanying drawings, as briefly described below.

FIG. 11 illustrates an example series of acts for embedding perturbation data via a machine learning model and filtering, aligning, and aggregating the embeddings in accordance with one or more embodiments.

FIG. 12 illustrates an example series of acts for determining a similarity measure between cell perturbation embeddings in response to a similarity query and generating a query response in accordance with one or more embodiments.

FIG. 13 illustrates an example series of acts for generating graphical user interfaces for display of perturbation heatmaps on a client device in accordance with one or more embodiments.

DETAILED DESCRIPTION

Figure 1:
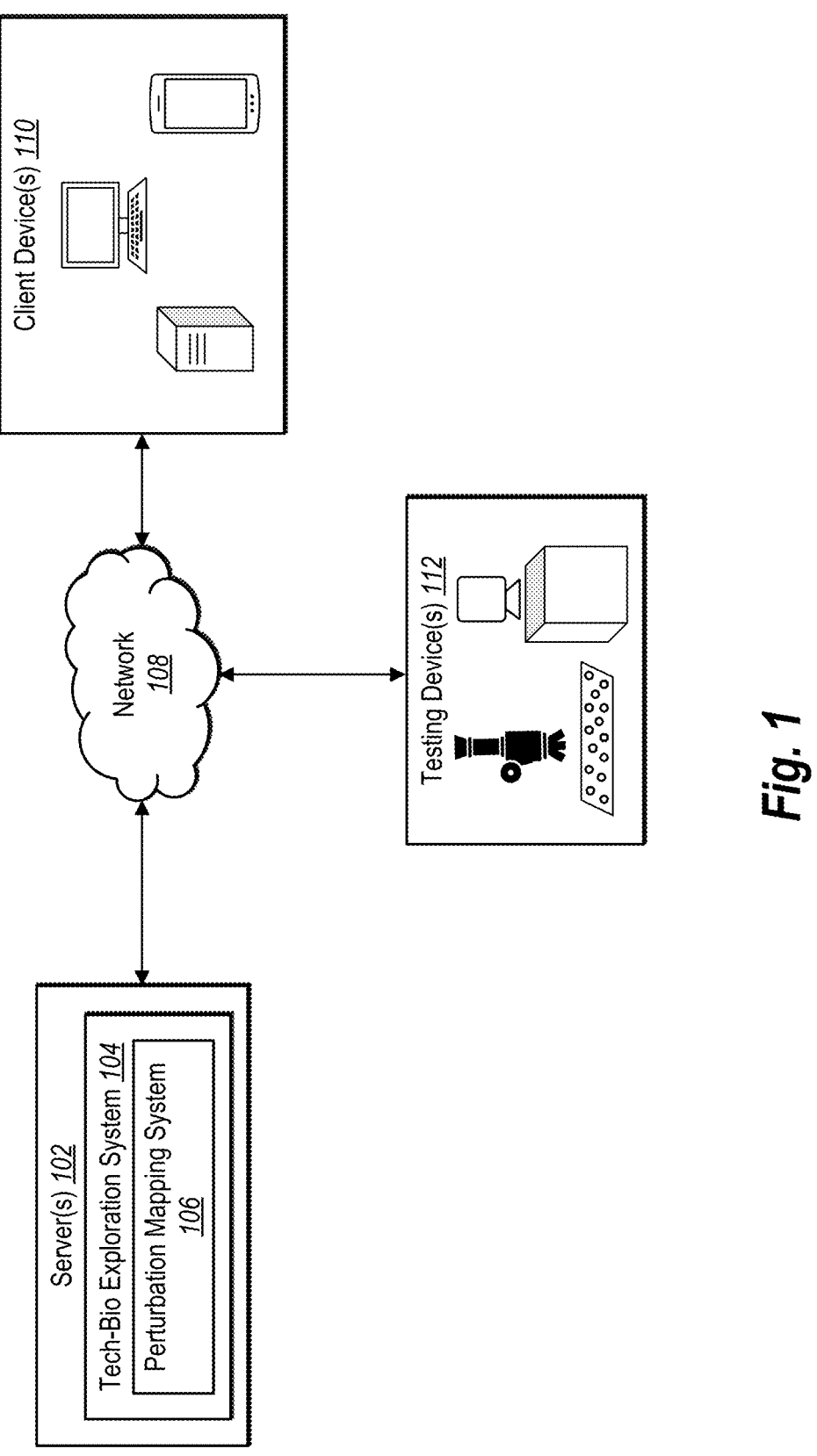
FIG. 1 illustrates a schematic diagram of a system environment in which a perturbation mapping system can operate in accordance with one or more embodiments.

This disclosure describes one or more embodiments of a perturbation mapping system that synthesizes perturbation data by embedding perturbation images via a machine learning model and filtering, aligning, and aggregating the embeddings to generate a genome-wide perturbation database for real-time generation of perturbation heatmap interfaces. In particular, the perturbation mapping system can synthesize biological perturbation data (e.g., phenomic digital images portraying cells resulting from various perturbations), by embedding the data into a low dimensional feature space via a machine learning model. Furthermore, in one or more implementations, the perturbation mapping system applies filtering, alignment, and aggregation models to generate accurate perturbation-level representations for compilation into a perturbation database. Indeed, utilizing this approach, the perturbation mapping system can accurately relate machine learning embeddings from any number of perturbation experiments for flexible comparison and analysis. Further, the perturbation mapping system can identify perturbation relationships by accessing the database, in response to a query of one or more perturbations, and determine a similarity measure between machine learning embeddings of the queried perturbations and the perturbations of the database. Additionally, the perturbation mapping system can generate, for display on a client device, an interactive heatmap of the identified perturbation relationships along with additional user interface elements for dynamic and efficient analysis.

As mentioned above, the perturbation mapping system can synthesize biological perturbation data, such as cell images, by embedding the data into a low dimensional space via a machine learning model (e.g., a convolutional neural network). Further, the perturbation mapping system can filter out perturbation embeddings according to one or more quality criterion. Additionally, the perturbation mapping system can align the perturbation embeddings across many perturbation experiments (e.g., hundreds or thousands of experiments) to accurately relate the embeddings across various assays and address various sources of inaccuracies such as batch effects. Moreover, the perturbation mapping system can aggregate the embeddings from a variety of experiments according to the perturbations to generate a single perturbation-level embedding for each perturbation. In addition, the perturbation mapping system can generate a genome-wide perturbation database by compiling the perturbation embeddings from a large array of perturbation experiments.

Further, as mentioned previously, the perturbation mapping system can identify perturbation relationships by accessing the database of embeddings, in response to a query of one or more perturbations. For example, the perturbation mapping system can generate a perturbation dataframe and a corresponding metadata dataframe including the metadata associated with each perturbation. Further, the perturbation mapping system can identify the queried perturbations in the metadata dataframe and access the corresponding perturbation embeddings in the perturbation dataframe for comparison with the perturbation embeddings of the database. Moreover, the perturbation mapping system can determine a similarity measure, such as a cosine similarity or feature space distance measurement, between the queried perturbations and/or between other embeddings of the database. The perturbation mapping system can then generate for display identified perturbation relationships, for example, in a two-dimensional perturbation heatmap.

As just mentioned, the perturbation mapping system can generate, an interactive perturbation heatmap of the identified perturbation relationships for display on a user interface of a client device. Indeed, the perturbation heatmap can display similarity measures between a plurality of perturbation embeddings corresponding to the queried perturbations and perturbations having an identified relationship with the queried perturbations. Additionally, the perturbation mapping system can generate the heatmap with various interactive user interface elements. For example, the perturbation mapping system can display an overlay element with additional information in response to an interaction with a similarity measure of the heatmap. Furthermore, the perturbation mapping system can generate additional data along with the perturbation heatmap for further analysis, such as a similarity distribution element, a gene information element, an enrichment element, and/or a projection/rejection element.

As mentioned above, although conventional systems can search and display digital biological relationship information, such systems have a number of problems in relation to accuracy, efficiency, and flexibility of operation. For instance, conventional systems inaccurately identify biological relationships arising from perturbations conducted across different experiments. Specifically, conventional systems require comparing results from multiple experiments, often conducted in varying conditions and even conducted by separate research groups at disparate times. Conventional systems cannot accurately relate biological signals from these multiple experiments and therefore often cannot correct for experiment specific variations. Because these systems display biological information based on isolated data, such relationships often inaccurately reflect the strength and/or nature of biological relationships.

In addition to their inaccuracies, conventional systems are also inefficient. More specifically, conventional systems require large numbers of interactions and queries of various digital databases/publications to identify biological relationships. Furthermore, conventional systems require additional inputs and user interfaces to review results and identify potential relationships. Indeed, conventional systems require a brute-force approach discovery approach that analyzes a disease model of interest and utilizes various user interactions, processes, and interfaces to screen pharmacological agents. The time, number of user interactions, and number of user interfaces required to search and review results through conventional systems wastes significant computing resources (e.g., memory and processing power). Moreover, these inefficiencies become more and more pronounced as the number of desired relationships and the size/number of pertinent digital information sources increases.

Furthermore, in addition to their inaccuracies and inefficiencies, conventional systems demonstrate operational inflexibility by lacking the ability to identify subtle biological perturbation relationships, such as those between genes and compounds (particularly in real-time). Indeed, the rigid query approaches utilized by conventional systems fail to provide real-time analysis of biological relationships. Moreover, conventional systems cannot flexibly respond to generate useful relationship analysis of client-selected perturbations (e.g., across various genes or compounds). Rather, conventional systems rigidly require client devices to review query results and compile comparisons across individual assays or experimental groups.

As suggested by the foregoing, the perturbation mapping system provides a variety of technical advantages relative to conventional systems. For example, by utilizing machine learning models to generate and align perturbation signals across experiments the perturbation mapping system improves accuracy relative to conventional systems. Specifically, the perturbation mapping system can align, filter, and aggregate perturbation signals from across disparate experiments to account for experiment specific variations. With filtered, aligned, and aggregated, machine learning embeddings, the perturbation mapping system can correct for cross-experiment differences and more accurately identify biological relationships between perturbations.

Furthermore, by generating a genome-wide perturbation database and generating perturbation heatmaps from the perturbation database, the perturbation mapping system improves efficiency relative to conventional systems. Specifically, the perturbation mapping system can compile perturbation data into a genome-wide perturbation database. Thus, the perturbation mapping system can eliminate the excessive interactions and queries of digital publications when accessing the database in response to receiving a query. Furthermore, the perturbation mapping system can generate for display, from the database, a user interface comprising a perturbation heatmap (reflecting similarity measures between queried perturbations) together with additional user interface elements for efficient analysis of particular perturbations and/or perturbation combinations. In one or more implementations, the perturbation mapping system generates a single user interface that includes a heatmap for visual comparison across a variety of queried perturbations, interactive heatmap elements for efficiently identifying perturbation information, user interface elements for controlling characteristics or features of the heatmap, and additional user interface elements for analyzing perturbations (such as a similarity distribution element, a gene information element, an enrichment element, and/or a projection/rejection element). Thus, the perturbation mapping system can significantly reduce the time, number of user interactions, and number of user interfaces needed for comparing and analyzing digital perturbation information relative to conventional systems.

Moreover, by comparing the perturbations in real time and identifying otherwise unidentifiable relationships, the perturbation mapping system can improve operational flexibility relative to conventional systems. Specifically, by generating and analyzing machine learning embeddings (e.g., embeddings of phenomic digital images across thousands of individual assays), the perturbation mapping system can identify subtle relationships that conventional systems cannot. Thus, the perturbation mapping system can generate insights to gain deeper understanding of genetic pathways, protein function, target identification, mechanism of action for small molecules, and potential therapeutic benefit of tested small molecules. Relationships can be confirmed through subsequent experimentation (i.e., testing a small molecule for efficacy against a disease model) and through orthogonal validation. Moreover, the perturbation mapping system can provide real-time responsiveness to a variety of perturbation queries. For example, client devices can provide queries of dozens of perturbations and the perturbation mapping system can generate (in real-time) similarity measures by comparing machine learning embeddings to flexibly generate and provide a perturbation heatmap indicating inter-relationships between the queried perturbations.

Additional detail regarding a perturbation mapping system 106 will now be provided with reference to the figures. In particular, FIG. 1 illustrates a schematic diagram of a system environment in which the perturbation mapping system 106 can operate in accordance with one or more embodiments.

As shown in FIG. 1, the environment includes server(s) 102 (which includes a tech-bio exploration system 104 and the perturbation mapping system 106), a network 108, client device(s) 110, and testing device(s) 112. As further illustrated in FIG. 1, the various computing devices within the environment can communicate via the network 108. Although FIG. 1 illustrates the perturbation mapping system 106 being implemented by a particular component and/or device within the environment, the perturbation mapping system 106 can be implemented, in whole or in part, by other computing devices and/or components in the environment (e.g., the client device(s) 110). Additional description regarding the illustrated computing devices is provided with respect to FIG. 14 below.

As shown in FIG. 1, the server(s) 102 can include the tech-bio exploration system 104. In some embodiments, the tech-bio exploration system 104 can determine, store, generate, and/or display tech-bio information including maps of biology, biology experiments from various sources, and/or machine learning tech-bio predictions. For instance, the tech-bio exploration system 104 can analyze data signals corresponding to various treatments or interventions (e.g., compounds or biologics) and the corresponding relationships in genetics, protenomics, phenomics (i.e., cellular phenotypes), and invivomics (e.g., expressions or results within a living animal). In one or more embodiments, the server(s) 102 comprises a data server. In some implementations, the server(s) 102 comprises a communication server or a web-hosting server.

For instance, the tech-bio exploration system 104 can generate and access experimental results corresponding to gene sequences, protein shapes/folding, protein/compound interactions, phenotypes resulting from various interventions or perturbations (e.g., gene knockout sequences or compound treatments), and/or invivo experimentation on various treatments in living animals. By analyzing these signals (e.g., utilizing various machine learning models), the tech-bio exploration system 104 can generate or determine a variety of predictions and inter-relationships for improving treatments/interventions.

To illustrate, the tech-bio exploration system 104 can generate maps of biology indicating biological inter-relationships or similarities between these various input signals to discover potential new treatments. For example, the tech-bio exploration system 104 can utilize machine learning and/or maps of biology to identify a similarity between a first gene associated with disease treatment and a second gene previously unassociated with the disease based on a similarity in resulting phenotypes from gene knockout experiments. The tech-bio exploration system 104 can then identify new treatments based on the gene similarity (e.g., by targeting compounds the impact the second gene). Similarly, the tech-bio exploration system 104 can analyze signals from a variety of sources (e.g., protein interactions, or invivo experiments) to predict efficacious treatments based on various levels of biological data.

The tech-bio exploration system 104 can generate GUIs comprising dynamic user interface elements to convey tech-bio information and receive user input for intelligently exploring tech-bio information. Indeed, as mentioned above, the tech-bio exploration system 104 can generate GUIs displaying different maps of biology that intuitively and efficiently express complex interactions between different biological systems for identifying improved treatment solutions. Furthermore, the tech-bio exploration system 104 can also electronically communicate tech-bio information between various computing devices.

As shown in FIG. 1, the tech-bio exploration system 104 can include a system that facilitates various models or algorithms for generating maps of biology (e.g., maps or visualizations illustrating similarities or relationships between genes, proteins, diseases, compounds, and/or treatments) and discovering new treatment options over one or more networks. For example, the tech-bio exploration system 104 collects, manages, and transmits data across a variety of different entities, accounts, and devices. In some cases, the tech-bio exploration system 104 is a network system that facilitates access to (and analysis of) tech-bio information within a centralized operating system. Indeed, the tech-bio exploration system 104 can link data from different network-based research institutions to generate and analyze maps of biology.

As shown in FIG. 1, the tech-bio exploration system 104 can include a system that comprises the perturbation mapping system 106 that generates, stores, manages, transmits, and analyzes cell perturbation datasets. For example, perturbation mapping system 106 can generate perturbation image embeddings (from phenomic digital images) utilizing a machine learning model and synthesize the embeddings according to various filtering, aligning, and aggregation models. Further, the perturbation mapping system 106 can determine similarities between cell perturbation embeddings and transmit query responses including the determined similarities. For example, the perturbation mapping system 106 can generate perturbation heatmaps including the determined similarities for display.

As used herein, the term "machine learning model" includes a computer algorithm or a collection of computer algorithms that can be trained and/or tuned based on inputs to approximate unknown functions. For example, a machine learning model can include a computer algorithm with branches, weights, or parameters that changed based on training data to improve for a particular task. Thus, a machine learning model can utilize one or more learning techniques (e.g., supervised or unsupervised learning) to improve in accuracy and/or effectiveness. Example machine learning models include various types of decision trees, support vector machines, Bayesian networks, random forest models, or neural networks (e.g., deep neural networks, generative adversarial neural networks, convolutional neural networks, recurrent neural networks, or diffusion neural networks). Similarly, the term "machine learning data" refers to information, data, or files generated or utilized by a machine learning model. Machine learning data can include training data, machine learning parameters, or embeddings/predictions generated by a machine learning model.

As also illustrated in FIG. 1, the environment includes the client device(s) 110. For example, the client device(s) 110 may include, but is not limited to, a mobile device (e.g., smartphone, tablet) or other type of computing device, including those explained below with reference to FIG. 14. Additionally, the client device(s) 110 can include a computing device associated with (and/or operated by) user accounts for the tech-bio exploration system 104. Moreover, the environment can include various numbers of client devices that communicate and/or interact with the tech-bio exploration system 104 and/or the perturbation mapping system 106.

Furthermore, in one or more implementations, the client device(s) 110 includes a client application. The client application can include instructions that (upon execution) cause the client device(s) 110 to perform various actions. For example, a user of a user account can interact with the client application on the client device(s) 110 to access tech-bio information, initiate a request for a perturbation similarity and/or generate GUIs comprising a perturbation similarity heatmap or other machine learning dataset and/or machine learning predictions/results.

As further shown in FIG. 1, the environment includes the network 108. As mentioned above, the network 108 can enable communication between components of the environment. In one or more embodiments, the network 108 may include a suitable network and may communicate using a various number of communication platforms and technologies suitable for transmitting data and/or communication signals, examples of which are described with reference to FIG. 14. Furthermore, although FIG. 1 illustrates computing devices communicating via the network 108, the various components of the environment can communicate and/or interact via other methods (e.g., communicate directly).

As mentioned previously, in one or more implementations, the perturbation mapping system 106 generates and accesses machine learning objects, such as results from biological assays. As shown, in FIG. 1, the perturbation mapping system 106 can communicate with testing device(s) 112 to obtain and then store this information. For example, the tech-bio exploration system 104 can interact with the testing device(s) 112 that include intelligent robotic devices and camera devices for generating and capturing digital images of cellular phenotypes resulting from different perturbations (e.g., genetic knockouts or compound treatments of stem cells). Similarly, the testing device(s) can include camera devices and/or other sensors (e.g., heat or motion sensors) capturing real-time information from animals as part of invivo experimentation. The tech-bio exploration system 104 can also interact with a variety of other testing device(s) such as devices for determining, generating, or extracting gene sequences or protein information.

Figure 2:
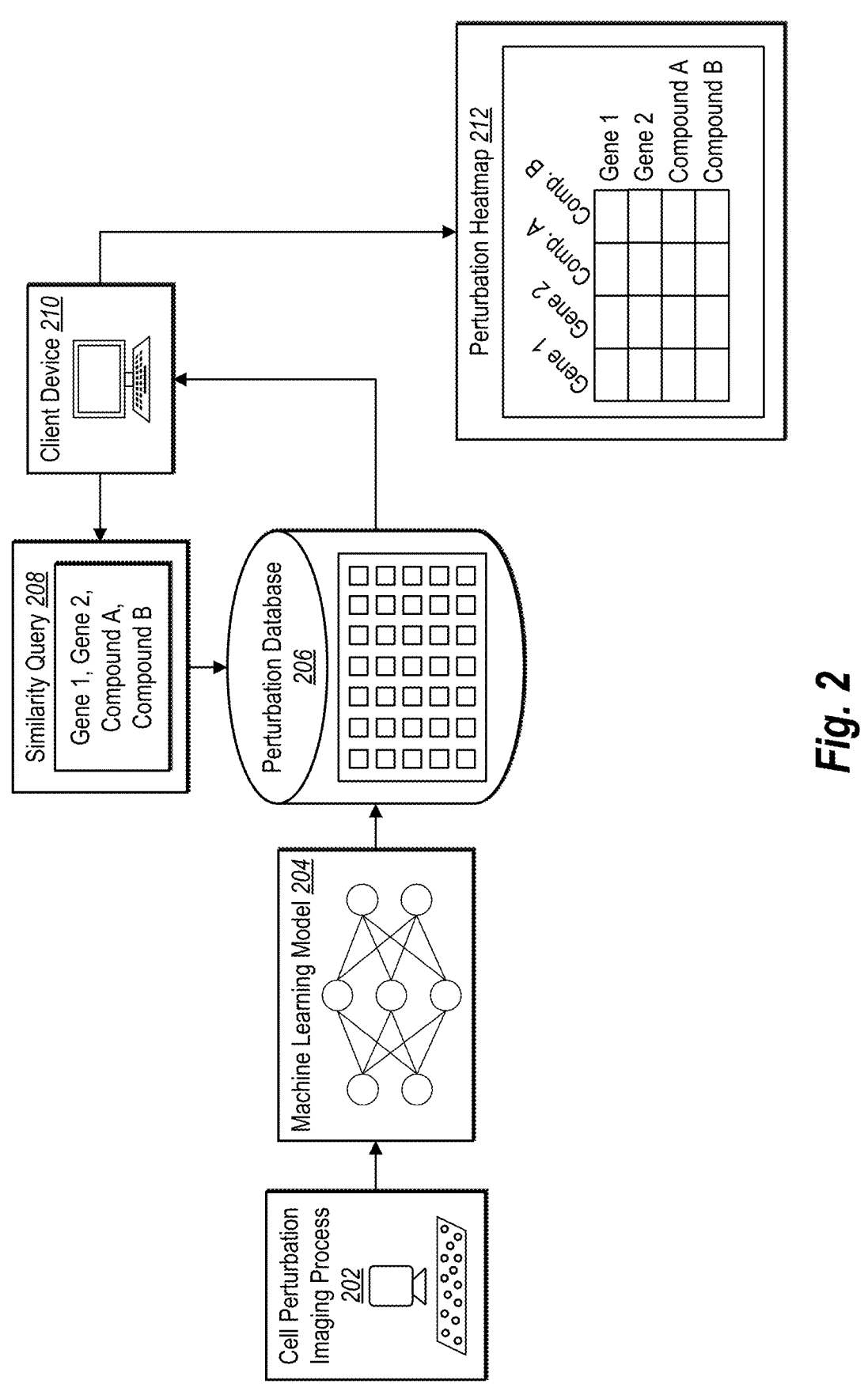
FIG. 2 illustrates embedding perturbation data to generate a genome-wide perturbation database for real-time generation of a perturbation heatmap in accordance with one or more embodiments.

As mentioned above, the perturbation mapping system 106 can embed perturbation data via a machine learning model to generate a genome-wide perturbation database for real-time generation of a perturbation heatmap. For example, FIG. 2 illustrates embedding perturbation data to generate a genome-wide perturbation database 206 for real-time generation of a perturbation heatmap 212 in accordance with one or more embodiments.

Specifically, in some embodiments, the perturbation mapping system 106 receives or generates phenomic digital images (i.e., perturbation images) representing cell perturbations from a cell perturbation imaging process 202. Additionally, the perturbation mapping system 106 generates the perturbation database 206 by embedding the perturbation images using a machine learning model 204. Further, the perturbation mapping system 106 receives a similarity query 208 including queried perturbations from a client device 210. In response to the similarity query 208, the perturbation mapping system 106 accesses the perturbation database 206 and determines a similarity measure between the cell perturbation embeddings of the queried perturbations of the similarity query 208 and the other perturbation embeddings of the database. Moreover, the perturbation mapping system 106 generates the perturbation heatmap 212 for display on the client device 210.

In one or more implementations, as mentioned previously, the perturbation mapping system 106 generates a perturbation database 206 by embedding the perturbation images using the machine learning model 204. For example, the perturbation mapping system 106 receives perturbation images representing cell perturbations from the cell perturbation imaging process 202.

For example, as used herein, the term "perturbation" (e.g., cell perturbation) refers to an alteration or disruption to a cell or the cell's environment (to elicit potential phenotypic changes to the cell). In particular, the term perturbation can include a gene perturbation (i.e., a gene-knockout perturbation) or a compound perturbation (e.g., a molecule perturbation or a soluble factor perturbation). These perturbations are accomplished by performing a perturbation experiment. A perturbation experiment refers to a process for a perturbation to a cell. A perturbation experiment also includes a process for developing/growing the perturbed cell into a resulting phenotype.

Thus, a gene perturbation can include gene-knockout perturbations (performed through a gene knockout experiment). For instance, a gene perturbation includes a gene-knockout in which a gene (or set of genes) is inactivated or suppressed in the cell (e.g., by CRISPR-Cas9 editing).

Moreover, the term "compound perturbation" can include a cell perturbation using a molecule and/or soluble factor. For instance, a compound perturbation can include reagent profiling such as applying a small molecule to a cell and/or adding soluble factors to the cell environment. Additionally, a compound perturbation can include a cell perturbation utilizing the compound or soluble factor at a specified concentration. Indeed, compound perturbations performed with differing concentrations of the same molecule/soluble factor can constitute separate compound perturbations. A soluble factor perturbation is a compound perturbation that includes modifying the extracellular environment of a cell to include or exclude one or more soluble factors. Additionally, soluble factor perturbations can include exposing cells to soluble factors for a specified duration wherein perturbations using the same soluble factors for differing durations can constitute separate compound perturbations.

As shown in FIG. 2, the perturbation mapping system 106 captures digital images of these different cell perturbations to generate perturbation images. As used herein, the term perturbation images (or phenomic digital images), refers to a digital image portraying a cell (e.g., a cell after applying a perturbation). For example, a perturbation image includes a digital image of a stem cell after application of a perturbation and further development of the cell. Thus, a perturbation image comprises pixels that portray a modified cell phenotype resulting from a particular cell perturbation.

Further, the perturbation mapping system 106 embeds the perturbation images into a low dimensional feature space via the machine learning model 204 (e.g., a convolutional neural network) to generate perturbation image embeddings. As used herein, the term "image embedding" (or perturbation embeddings, perturbation image embeddings or phenomic image embeddings) refers to a numerical representation of a perturbation image. For example, a perturbation embedding includes a vector representation of a perturbation image generated by a machine learning model (e.g., a convolutional neural network or other machine learning embedding model). Thus, a perturbation embedding includes a feature vector generated by application of various convolutional neural network layers (at different resolutions/dimensionality).

The perturbation mapping system 106 can generate image embeddings at different levels (e.g., different levels of detail). For example, in some implementations, the perturbation mapping system 106 captures digital images from a well of a perturbation experiment. As used herein, the term well refers depression or area of a plate used to conduct an experiment. For example, a well refers to a depression or cavity in a microplate or multi-well plate. A well can serve a testing or experimental chamber for samples, reagents, or substances. Thus, a well can hold one or more cells within a perturbation experiment.

The perturbation mapping system 106 can capture digital images of an entire well (e.g., at a well-level) or capture a digital image of a portion or patch of a well. As used herein, the term "patch" refers to a sub-part or portion of a well. For example, a patch-level image refers to a digital image portraying a portion (e.g., one-fourth or one-eighth) of a well.

The perturbation mapping system 106 can generate embeddings at different levels as well. For example, in some implementations, the perturbation mapping system 106 captures well-level images and divides the well-level images into patch-level images. The perturbation mapping system 106 utilizes the machine learning model 204 to generate patch-level image embeddings (i.e., embeddings representing a patch/portion of a well). In some implementations, the perturbation mapping system 106 captures well-level images and utilizes the well-level images to generate well-level image embeddings (i.e., embeddings representing a well).

Upon generating perturbation embeddings, the perturbation mapping system 106 synthesizes these perturbation embeddings by applying filtering models, alignment models, and/or aggregation models. As used herein, the term filtering model refers to a model that removes or filters data points. For example, a filtering model includes a computer-implemented model that removes digital images or embeddings from a dataset. To illustrate, a filtering model can apply one or more quality criterion and remove digital images or embeddings that fail to satisfy the quality criterion.

As used herein, the term "quality criterion" refers to a metric or measure of quality (e.g., of a digital image or embedding). For instance, quality criterion can include a measure of completeness, clarity, cell count, and/or consistency. Thus, for example, if a digital image of a well is blank, the perturbation mapping system 106 can apply the filtering model to remove the digital image (or corresponding embedding) from a dataset. Similarly, if an embedding at a particular fails to meet certain consistency metrics, the perturbation mapping system 106 can withhold or filter the embedding from a perturbation database.

As used herein, the term alignment model refers to a model that aligns or corrects datapoints. In particular, an alignment model includes a computer-implemented algorithm for aligning embeddings to remove artifacts, irregularities, or skewing factors, such as batch effects. The perturbation mapping system 106 can utilize a variety of alignment models, including centerscale (e.g., per-batch standardization), TVN (typical variation normalization), or other alignment approaches (e.g., nearest neighbor matching or conditional variational autoencoders). In one or more implementations, the perturbation mapping system 106 aligns datapoints utilizing a proximity bias model.

As used herein, the term aggregation model refers to a computer-implemented model for combining or aggregating data points. For example, an aggregation model includes a computer-implemented model for combining or aggregating embeddings (e.g., perturbation image embeddings). Thus, an aggregation model can transform embeddings from one level to another level. To illustrate, an aggregation model can combine a plurality of patch-level embeddings from a well to generate well-level embeddings. Moreover, an aggregation model can combine a plurality of well-level embeddings for a particular perturbation to generate perturbation-level embeddings (i.e., an embedding representing a perturbation generated by combining individual well-level embeddings representing a shared perturbation). Similarly, the aggregation model can generate experiment-level embeddings (e.g., by combining well-level embeddings for a particular experiment).

Thus, in one or more implementations, the perturbation mapping system 106 applies filtering models, alignment models, and/or aggregation models (in various orders) to generate accurate perturbation-level embeddings. The perturbation mapping system 106 can then compile these perturbation level representations into the perturbation database 206. Additional detail regarding generating perturbation-level embeddings and a perturbation database will be discussed in further detail with respect to FIGS. 3A and 3B.

As mentioned above, in some embodiments, the perturbation mapping system 106 receives the similarity query 208 including queried perturbations from the client device 210. As used herein, the term similarity query refers to a query (from a client device) for comparative information regarding one or more perturbations. In particular, a similarity query includes a query from a client device for similarity measures between perturbations (e.g., between genes, between compounds, and/or between a gene and a compound). Indeed, the similarity query 208 can include one or more perturbations (e.g., gene perturbations or compound perturbations) for determination of a similarity measure between the embeddings of the queried perturbations and the embeddings of perturbations in the perturbation database 206.

As used herein, the term "similarity measure" refers to a metric or value indicating likeness, relatedness, or similarity. For instance, a similarity measure includes a metric indicating relatedness between two perturbations (e.g., between two perturbation image embeddings). To illustrate, the perturbation mapping system 106 can determine a similarity measure by comparing two feature vectors representing phenomic digital images. Thus, a similarity measure can include a cosine similarity between feature vectors or a measure of distance (e.g., Euclidian distance) in a feature space.

For instance, as illustrated in FIG. 2, the similarity query 208 can include gene perturbations (e.g., Gene 1 and Gene 2) and compound perturbations (e.g., Compound A and Compound B). In response to the similarity query 208, the perturbation mapping system 106 can then determine a similarity measure between perturbation embeddings corresponding to the queried genes and compounds (e.g., for Gene 1, Gene 2, Compound A, and Compound B) from the perturbation database 206. Specifically, the perturbation mapping system 106 access the gene perturbation image embeddings for Gene 1 and Gene 2, access the compound perturbation image embeddings for Compound A and Compound B, and compares the various embeddings to determine similarity measures.

Although FIG. 2 illustrates determining similarity measures for perturbations identified in the similarity query 208, the perturbation mapping system 106 can also determine similarity measures between the queried perturbations and other perturbations. For example, in some implementations, the perturbation mapping system 106 compares perturbation image embeddings for the queried perturbations with additional perturbation image embeddings from the perturbation database 206. Indeed, the perturbation mapping system 106 can compare the queried perturbation embeddings with these additional perturbation image embeddings, determine similarity measures, and surface particular selected perturbations based on the similarity measures (e.g., surface those perturbations with the highest similarity measures).

Thus, the perturbation mapping system 106 an perform a perturbation comparison utilizing image embeddings (e.g., perturbation-level image embeddings). As used herein, a perturbation comparison refers to a representation comprising a comparison between two perturbations. In particular, a perturbation comparison can include a visual representation (e.g., graphical user interface element) indicating a comparison between two perturbations (e.g., indicating a comparison of perturbation image embeddings). Thus, for example, a perturbation comparison can include a chart or graph indicating two related perturbations (e.g., two perturbations having similarity measures that surpass a threshold similarity). A perturbation comparison can also include a visual representation of similarity measures. Indeed, in one or more implementations, a perturbation comparison includes a perturbation heatmap.

As used herein, a perturbation heatmap includes an array, table, or graphical illustration with cells representing similarity measures between perturbations. For example, a perturbation heatmap includes a table with cells representing similarity measures at the intersection of rows representing a first set of perturbations and columns representing a second set of perturbations. Thus, a perturbation heatmap includes a table where rows represent individual perturbations, columns represent individual perturbations, and cells are colored to represent similarity measures for the corresponding perturbations.

For example, as shown in FIG. 2, the perturbation mapping system 106 generates the perturbation heatmap 212 and provides the perturbation heatmap 212 for display on the client device 210. For instance, as shown in FIG. 2, the perturbation mapping system 106 generates the perturbation heatmap 212 as an interactive user interface element indicating the perturbation relationships for the queried perturbations Gene 1, Gene 2, Compound A, and Compound B. The perturbation mapping system 106 can provide the perturbation heatmap 212 (and/or other perturbation comparisons) as part of a query response to a client device.

As used herein, the term query response refers to a response to a query from a client device. In particular, a query response includes a response to a similarity query that includes similarity measures between perturbations. Thus, the perturbation mapping system 106 can transmit a query response that includes similarity measures (e.g., in the form of a perturbation comparison, such as data for a perturbation heatmap).

Although FIG. 2 illustrates the perturbation heatmap 212 including similarity measures between the queried perturbations Gene 1, Gene 2, Compound A, and Compound B, as just mentioned, the perturbation mapping system 106 can also display other relationship information. For example, the perturbation mapping system 106 can also identify and display similarity measures between additional perturbations for a Gene 4 and a Gene 5 and compound perturbations for a Compound 4, a Compound 5, and a Compound 6 (e.g., the genes/compounds with the highest similarity measures relative to the queried perturbations). Additionally, the perturbation mapping system 106 can generate, for display on the user device, graphical user interfaces including additional data along with the interactive perturbation heatmap 212 for further analysis as will be further discussed with respect to FIGS. 6A-10.

Moreover, in one or more embodiments, the perturbation mapping system 106 can incorporate perturbation data from a large array of perturbation experiments. Indeed, the perturbation mapping system 106 can incorporate perturbation data (e.g., perturbation images) into the perturbation database 206 from perturbation experiments from disparate perturbation experiments, such as perturbation experiments conducted at different times and by different research groups. For example, the perturbation mapping system 106 can update the perturbation database 206 regularly with additional perturbation data from ongoing perturbation experiments as discussed in greater detail with respect to FIG. 4.

Figure 3A:
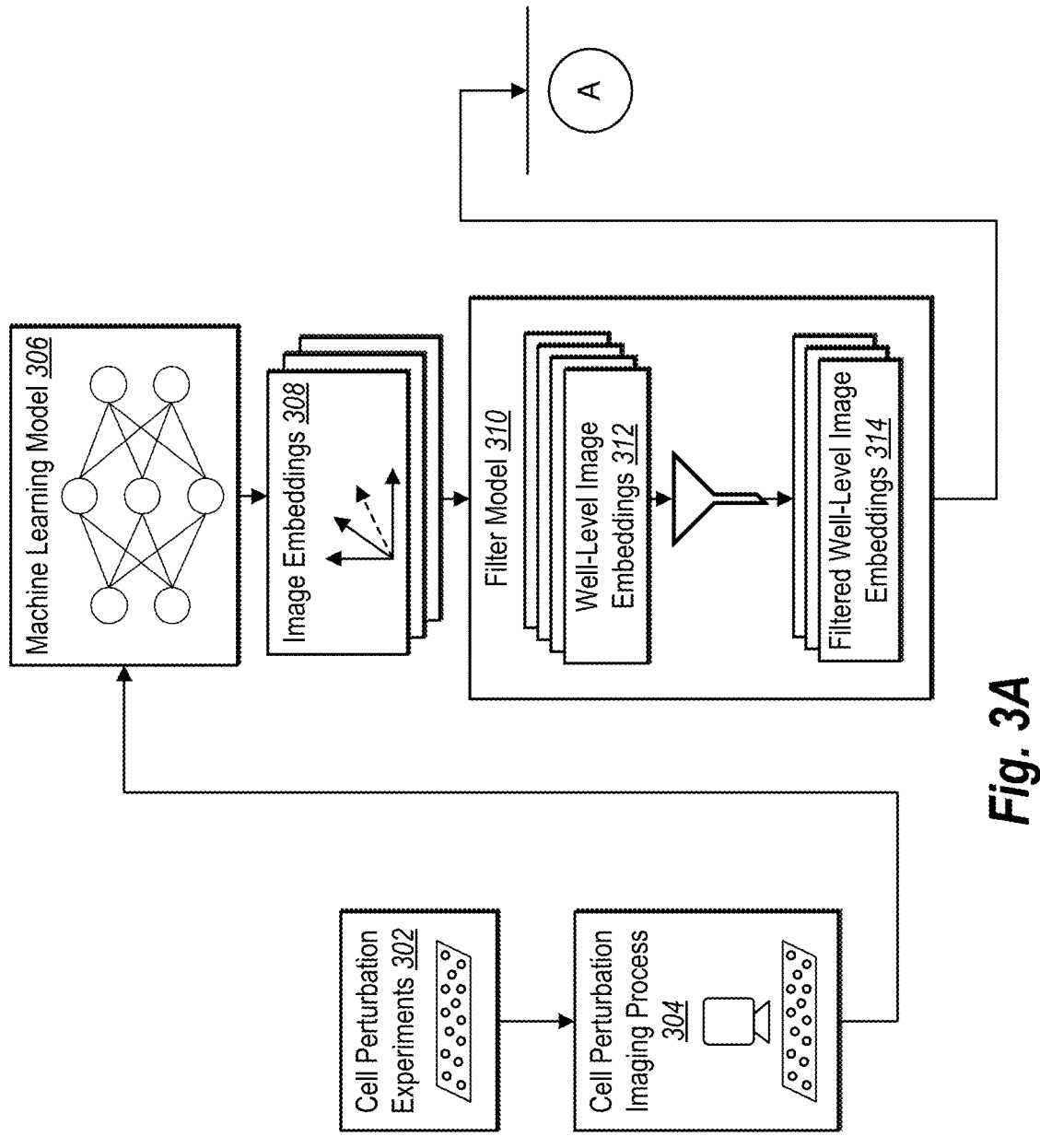
FIGS. 3A and 3B illustrate generating a perturbation database by utilizing a machine learning model to embed cell perturbation images into a low dimensional space and applying various filtering, aligning, and aggregation models to the perturbations in accordance with one or more embodiments.
Figure 3B:
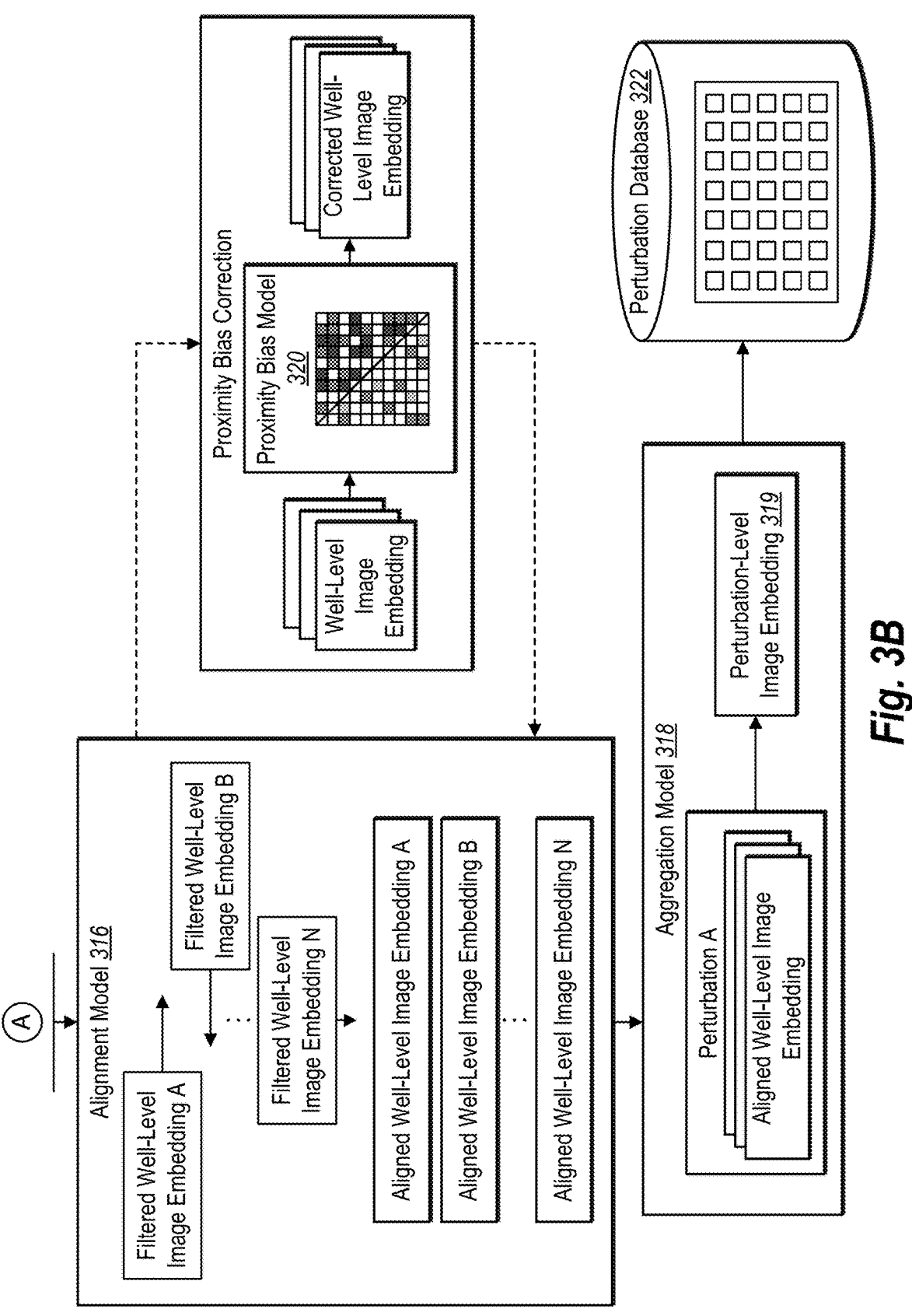

As mentioned above, the perturbation mapping system 106 can embed perturbation images using a machine learning model and apply various filtering, aligning, and aggregation models to generate a perturbation database. For example, FIGS. 3A and 3B illustrate generating a perturbation database 322 by utilizing a machine learning model 306 to embed cell perturbation images into a low dimensional space and applying various filtering, aligning, and aggregation models to the perturbations in accordance with one or more embodiments. Specifically, FIGS. 3A and 3B show the perturbation mapping system 106 receiving or accessing cell perturbation images from a cell perturbation imaging process 304 that generates images from cell perturbation experiments 302. Further, the perturbation mapping system 106 generates an image embedding 308 (e.g., a patch-level image embedding or well-level image embedding 312) for each cell perturbation image utilizing the machine learning model 306. Additionally, the perturbation mapping system 106 filters each well-level image embedding 312 according to one or more quality criterion. Moreover, the perturbation mapping system 106 applies a statistical aligning model to each filtered well-level image embedding 314 to align the filtered well-level image embeddings. Furthermore, the perturbation mapping system 106 applies an aggregation model 318 to the aligned well-level image embeddings to generate a perturbation-level image embedding 319 for each perturbation. Also, the perturbation mapping system 106 compiles the perturbation-level image embeddings into the perturbation database 322.

As mentioned above, the perturbation mapping system 106 receives cell perturbation images from the cell perturbation imaging process 304 that generates digital image from the cell perturbation experiments 302. For example, the perturbation mapping system 106 performs the cell perturbation experiments 302 by applying different cell perturbations to different cells in wells of different plates. Thus, for example, a first well can include stem cells with gene perturbations (e.g., CRISPR knockout of a particular gene) and a second well can include cells with compound perturbations (e.g., application of a particular drug). Thus, for example, the perturbation mapping system 106 performs perturbation experiments that include thawing cells, plating them, transfection (for CRISPR-treated wells), adding compounds or soluble factors, fixation, staining, and imaging. For example, the perturbation mapping system 106 can utilize a high-dimensional digital camera to capture digital images of cells portraying different phenotypes resulting from the different perturbations. These phenomic digital images thus illustrate the resulting cellular effects of the underlying perturbations.

The perturbation mapping system 106 can capture and analyze phenomic digital images in a variety of ways. For example, in some implementations, the perturbation mapping system 106 captures and/or utilizes digital images of a well portraying phenotypes resulting from cell perturbations. In some implementations, the perturbation mapping system 106 captures and/or utilizes digital images portraying a portion of a well (e.g., a percentage or pre-defined portion of a well). To illustrate, the perturbation mapping system

106 can capture (or generate by dividing well-level images) patch images portraying portions of slide plate wells containing perturbed cells. Thus, for example, a first patch image portrays a top left corner of a well and a second patch image portrays a bottom left corner of a well, etc.

The perturbation mapping system 106 can repeatedly perform the cell perturbation experiments 302 and/or the cell perturbation imaging process 304. For example, in some implementations, the perturbation mapping system 106 performs these acts millions of times (per week) to generate digital images portraying perturbations from consistent experimental protocols that can then be compared for determining relationships between the underlying genes and/or compounds at issue. Thus, the perturbation mapping system 106 can receive perturbation images from a plurality of wells corresponding to a plurality of cell perturbations. Additionally, the wells can be located on a plurality of plates and from a plurality of separate perturbation experiments.

As shown in FIG. 3A, the perturbation mapping system 106 generates image embeddings (e.g., patch-level image embeddings or well-level image embeddings) utilizing the machine learning model 306. Indeed, in one or more embodiments, the perturbation mapping system 106 generates a patch-level image embedding for each patch image utilizing the machine learning model 306 and/or a well-level image embedding for each well image utilizing the machine learning model 306.

The perturbation mapping system 106 can utilize a variety of machine learning models to generate the image embeddings 308. For instance, in some embodiments, the perturbation mapping system 106 utilizes a deep image embedding model (e.g., a neural network such as a convolutional neural network.

For example, upon capturing phenomic digital images, the perturbation mapping system 106 utilizes a deep image embedding model to generate phenomic image embeddings. For instance, a deep image embedding model includes a neural network (e.g., a convolutional neural network) or other embedding model that generates a vector representation of an input digital image.

In some implementations, the perturbation mapping system 106 trains the deep image embedding model through supervised learning (e.g., to predict perturbations from digital images). For instance, the perturbation mapping system 106 trains the deep image embedding model to generate predicted perturbations from phenomic digital images. For instance, perturbation mapping system utilizes neural network layers to generate vector representations of the phenomic digital images at different levels of abstraction and then utilizes output layers to generate predicted perturbations. The perturbation mapping system 106 then trains the deep image embedding model by comparing the predicted perturbations with ground truth perturbations. Although the foregoing example describes a particular training approach and embedding model, the perturbation mapping system 106 can utilize a variety of image embedding models.

With regard to FIG. 3A, the perturbation mapping system 106 utilizes the machine learning model 306 to generate embeddings (e.g., feature/vector representations) of new phenomic digital images. For instance, the perturbation mapping system 106 utilizes the internal neural network layers to generate embeddings (rather than generate perturbation predictions). The perturbation mapping system 106 then utilizes the embeddings as representations of the phenomic digital images.

Thus, utilizing the convolutional neural network, the perturbation mapping system 106 can embed each image into a low dimensional feature space. Indeed, the perturbation mapping system 106 can generate a multi-dimensional representation of each image within the low dimensional feature space. These multi-dimensional representations thus represent the features of different underlying perturbations (e.g., genes and compounds) as reflected in phenomic digital images utilized to generate the embeddings.

As mentioned, the perturbation mapping system 106 can combine these embeddings through various filtering, aggregation, and alignment models. For example, FIG. 3A illustrates the perturbation mapping system 106 filtering well-level image embeddings 312 according to one or more quality criterion. For example, the perturbation mapping system 106 applies a filter model 310 to filter each well-level image embedding 312 according to one or more quality criterion. In particular, the perturbation mapping system 106 utilizes quality criteria in the filtration model to filter outlier image embeddings. For instance, the perturbation mapping system 106 identifies and removes image embeddings that may correspond to images having unusually high intensity or that appear to be empty.

Although FIG. 3A illustrates applying the filter model 310 to the well-image embeddings 312 it will be appreciated that the perturbation mapping system 106 can apply the filter model to patch-level image embeddings and/or to phenomic digital images directly. For example, in some implementations, the perturbation mapping system 106 applies the filter model 310 directly to perturbation images prior to embedding the images via the convolutional neural network. Moreover, in some implementations, the perturbation mapping system 106 applies the filter model 310 to patch-level image embeddings (rather than the well-level image embeddings 312).

Thus, in one or more implementations, the perturbation mapping system 106 receives a first perturbation image portraying a first cell resulting from a first gene knockout perturbation of a first gene or a first compound perturbation. Moreover, the perturbation mapping system 106 receives a second perturbation image portraying a second cell resulting from a second gene knockout perturbation of a second gene or a second compound perturbation. The perturbation mapping system 106 generates, utilizing the machine learning model 306, a plurality of well-level image embeddings. In particular, the perturbation mapping system 106 generates, utilizing a convolutional neural network, a first well-level embedding for the first perturbation image and a second well-level embedding for the second perturbation image.

In one or more embodiments, the perturbation mapping system 106 applies the filter model 310 after aggregating one or more embeddings. For example, as described in greater detail below (with respect to FIG. 3B), the perturbation mapping system 106 can apply an aggregation model to patch-level image embeddings to generate the well-level image embeddings 312. Thus, rather than accessing or receive well-level image embeddings directly from the cell perturbation imaging process 304 the perturbation mapping system 106 can also receive or access patch-level image embeddings and aggregate the patch-level image embeddings to generate the well-level image embeddings 312.

In some implementations, the perturbation mapping system 106 applies the filter model 310 to well-level and/or perturbation-level image embeddings based on consistency criteria. For example, the perturbation mapping system 106 can apply a phenoprint filter/consistency filter to ensure that vector representations for a particular perturbation are consistently providing reliable information. For example, in one or more implementations, the perturbation mapping system 106 filters out embeddings (utilizing a phenoprint filter), if vector representations of different guides for a gene are not consistently pointing to the same direction in the perturbation representation space.

To illustrate, in some implementations, the perturbation mapping system 106 defines the center of the perturbation feature space relative to non-coding intron genes. Thus, the center of the space is the center of a certain number of intron wells (e.g., phenomic images resulting from cell perturbations corresponding to these introns). Accordingly, the perturbation embeddings are defined relative to how the introns appear in the embedding space. Accordingly, genes can be flagged utilizing the phenoprint filter if the resulting vector representations fail to satisfy a threshold consistency (e.g., fail to point within a threshold direction) relative to the center of the embedding space.

As mentioned, the perturbation mapping system 106 can also align image embeddings. For example, FIG. 3B illustrates the perturbation mapping system 106 applying a statistical aligning model to each filtered well-level image embedding 314 to align the filtered well-level image embeddings. Specifically, in one or more embodiments, the perturbation mapping system 106 can utilize an alignment model 316 to align the filtered well-level image embeddings to generate aligned well-level image embeddings.

For example, the perturbation mapping system 106 can utilize various models to reduce or eliminate non-biological sources of variation in data. For instance, the perturbation mapping system 106 can utilize various. normalization approaches such quantile normalization or TMM normalization. Moreover, the perturbation mapping system 106 can utilize match effect removal models, such as ComBat or Surrogate Variable Analysis.

In one or more implementations, the perturbation mapping system 106 utilize a baseline approach for aligning perturbation units by using control units in each batch to center and scale features in each set. For example, the perturbation mapping system 106 can include a control unit of the same cell/perturbation combination in each batch. The perturbation mapping system 106 can then align each batch by aligning the control unit across batches. Thus, the perturbation mapping system 106 can utilize a variety of alignment models, including centerscale (e.g., per-batch standardization) or TVN (typical variation normalization). For example, the perturbation mapping system 106 can utilize the alignment model 316 to align well-level image embeddings across perturbation experiments.

Thus, the perturbation mapping system 106 can analyze a plurality of image embeddings (e.g., well-level image embeddings) to generate aligned well-level image embeddings. Specifically, in one or more implementations, the perturbation mapping system 106 aligns a set of well-level image embeddings from a plurality of different perturbation experiments (having a shared perturbation) according to a statistical aligning model, as described above.

Also, in one or more implementations, generating the aligned well-level image embeddings can include utilizing a proximity bias model 320 to generate proximity bias corrected well-level image embeddings. Proximity bias, as used herein, refers to a bias or skewing resulting from CRISPR gene knockouts. In particular, proximity bias includes the systematic phenotypic similarity of CRISPR-Cas9 knockouts to knockouts of biologically unrelated genes on the same chromosome arm. For example, the distribution of similarities (e.g., cosine similarities) for relationships between genes on the same chromosome is shifted relative to the distribution of similarities for gene pairs on different chromosomes. The proximity bias model 320 can correct for proximity bias utilizing a vector representation of the proximity bias. In particular, the proximity bias model 320 can determine a vector representation of unexpressed genes of a chromosome arm (e.g., image embeddings of the unexpressed genes) and utilize the vector representation to correct for proximity bias. For instance, the proximity bias model 320 can apply the vector correction representation to an image embedding to generate a corrected image embedding. To illustrate, in one or more implementations, the proximity bias model 320 determines and subtracts a mean vector for unexpressed genes of a chromosome arm from each gene representation (e.g., well-level image embedding) on that arm. Indeed, in one or more embodiments, the perturbation mapping system 106 can utilize a proximity bias model as described in *High-Resolution Genome-wide Mapping of Chromosome-arm-scale Truncation Induced by CRISPR-Cas9 Editing* published in bioRxiv on Apr. 15, 2023, the contents of which are herein incorporated by reference in their entirety. Accordingly, the perturbation mapping system 106 can utilize the proximity bias model 320 to generate proximity bias corrected well-level image embeddings.

By utilizing the proximity bias model 320, the perturbation mapping system 106 can generate corrected image embeddings (e.g., corrected well-level image embeddings and ultimately corrected perturbation-level image embeddings). Thus, the perturbation mapping system 106 can generate, utilizing the proximity bias model 320, proximity bias corrected perturbation-level image embeddings. Moreover, as described in greater detail below, the perturbation mapping system 106 can also generate perturbation comparisons from the proximity bias corrected perturbation-level image embeddings.

Furthermore, as mentioned above, in some implementations the perturbation mapping system 106 can apply the aggregation model 318 to the aligned well-level image embeddings to generate the perturbation-level image embedding 319 for each perturbation. Indeed, each perturbation can include at least several biological replicates within an experiment, resulting in replicate well-level image embeddings for each perturbation. Additionally, disparate perturbation experiments may also include replicate perturbations resulting in additional well-level image embeddings for each perturbation. Once the perturbation mapping system 106 aligns these replicates, as described above, the perturbation mapping system 106 can then apply the aggregation model 318 to the aligned well-level image embeddings to generate the perturbation-level image embedding 319 for each perturbation.

The perturbation mapping system 106 can utilize a variety of aggregation approaches. In some implementations, the perturbation mapping system 106 utilizes a mean or averaging approach. For example, the perturbation mapping system 106 determines feature vectors (e.g., well-level image embeddings) and averages the feature vectors for a particular perturbation to generate a perturbation-level image embedding. Thus, in some implementations, the perturbation mapping system 106 can utilize an aggregation model that calculates the mean adjusted well-level image embeddings to generate the perturbation-level image embeddings. The perturbation mapping system 106 can utilize other aggregation approaches. For example, the perturbation mapping system 106 can also utilize a weighted combination approach (e.g., that weights different embeddings differently based on features or characteristics, such as recency, image quality, image source, etc.). Similarly, the perturbation mapping system 106 can utilize other statistical aggregation models.

In one or more implementations, the perturbation mapping system 106 also updates the perturbation database with updated embeddings (e.g., upon capturing additional perturbation images and generating additional perturbation image embeddings). For instance, the perturbation mapping system 106 can receive an additional plurality of perturbation images portraying additional cells. In response, the perturbation mapping system 106 can generate, utilizing the machine learning model 306, an additional plurality of well-level image embeddings. Moreover, the perturbation mapping system 106 can generate modified perturbation-level image embeddings from the additional plurality of well-level image embeddings and the (original) well-level image embeddings. In particular, the perturbation mapping system 106 can combine the original well-level image embeddings and the additional (new) well-level image embeddings by utilizing the alignment model 316 and the aggregation model 318 (as described above).

Additionally, the perturbation mapping system 106 can compile the perturbation-level image embeddings into the perturbation database 322. For instance, in one or more embodiments, the perturbation mapping system 106 utilizes various APIs to compile the perturbation-level image embeddings into the perturbation database 322 for use in generating perturbation comparisons. Furthermore, in one or more embodiments, the perturbation mapping system 106 can utilize varying versions of the models described above (e.g., the filter model 310, the alignment model 316, the aggregation model 318, the proximity bias model 320), or may eliminate, reorder, or repeat one or more of these models to generate perturbation embeddings for compilation into the database.

Indeed, in one or more implementations, the perturbation mapping system 106 performs a different order than illustrated in FIGS. 3A-3B by first aligning, then filtering, then aggregating. Similarly, in some implementations, the perturbation mapping system 106 applies multiple different aggregation processes. For example, the perturbation mapping system 106 can aggregate from guide-level to gene-level embeddings. Similarly, the perturbation mapping system 106 can aggregate across experiment repeats. Moreover, the perturbation mapping system 106 can apply filter models multiple times, at different stages, utilizing different filter criterion.

Figure 4:
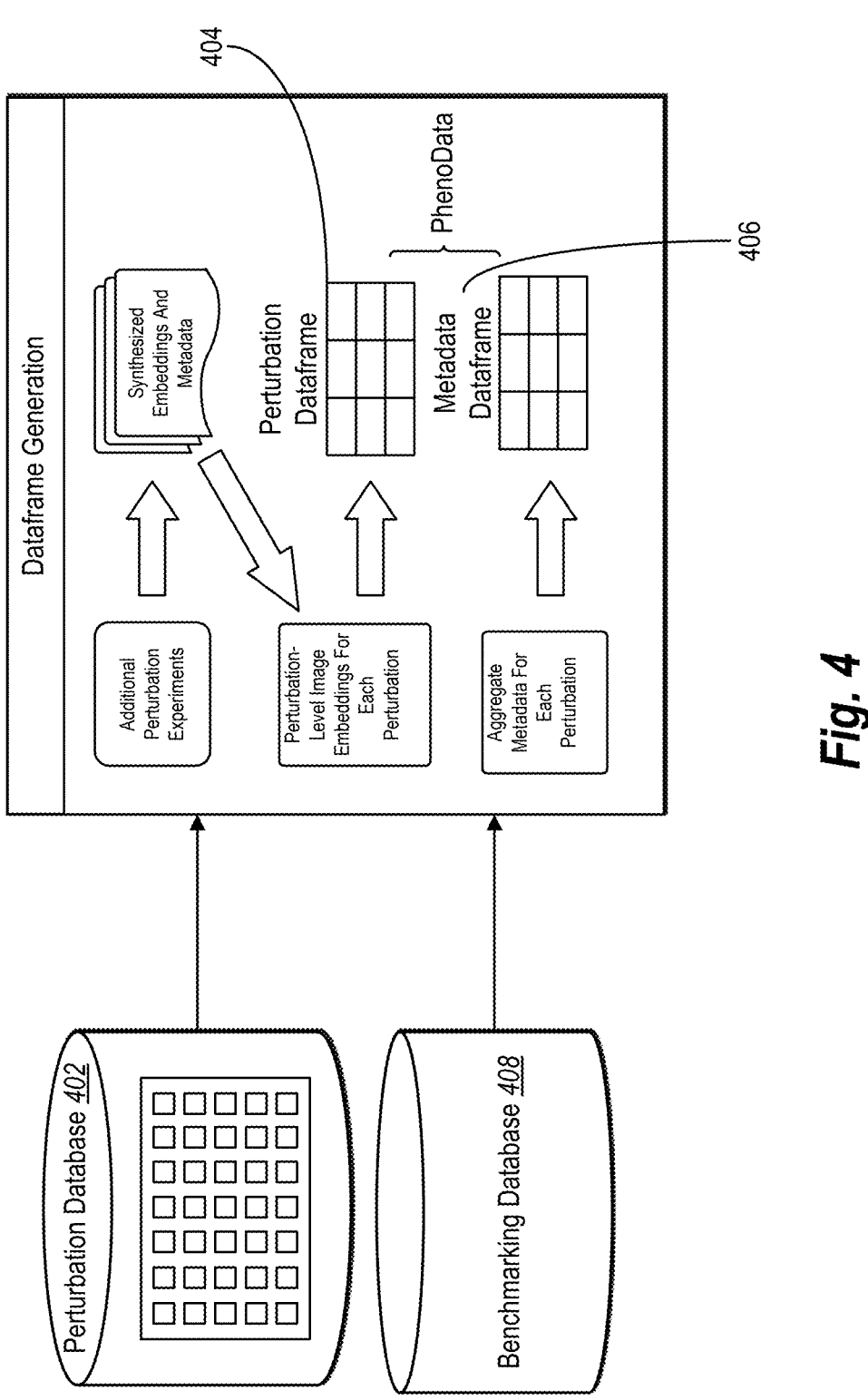
FIG. 4 illustrates generating a perturbation dataframe and a metadata dataframe from a perturbation database in accordance with one or more embodiments.

Moreover, the perturbation mapping system 106 can generate and aggregate metadata associated with perturbation embeddings. Indeed, the perturbation mapping system 106 can generate perturbation and metadata dataframes from a perturbation database to facilitate accessing the cell image embeddings (e.g., the perturbation-level image embeddings, etc.) when generating perturbation comparisons. For example, FIG. 4 illustrates generating a perturbation dataframe 404 and a metadata dataframe 406 from a perturbation database 402 in accordance with one or more embodiments. Specifically, the perturbation mapping system 106 can generate the perturbation dataframe 404 which can include the cell image embeddings, such as the perturbation-level image embeddings for each cell perturbation. Further, the perturbation mapping system 106 can generate the metadata dataframe 406 which can include the metadata corresponding to the cell image embeddings. Additionally, the perturbation mapping system 106 can regularly update the perturbation dataframe 404 and the metadata dataframe 406 with new cell image embeddings and their corresponding metadata as the perturbation mapping system 106 incorporates this new data into the database.

As used herein, the term dataframe refers to a data structure for storing and organizing digital information. In particular, a dataframe includes a tabular data structure organized into rows and columns. Thus, for example, a dataframe can include a two-dimensional data structure that includes digital image embeddings for different perturbations and/or metadata corresponding to the different perturbations. As used herein, metadata refers to contextual information regarding a digital representation of information. For example, metadata includes contextual information regarding a perturbation image embedding, such as information regarding the underlying perturbation experiment, perturbation, and perturbation image. To illustrate, metadata can include date/time information regarding a perturbation experiment or image capture, well information, plate information, cell type information, experimental details, etc.

As mentioned previously, in one or more implementations, the perturbation mapping system 106 can generate the perturbation dataframe 404 which can include the cell image embeddings, such as the perturbation-level image embeddings for each cell perturbation. For example, the perturbation mapping system 106 can aggregate initial cell image embeddings according to perturbation to generate cell image embeddings stored in the perturbation dataframe 404. In particular, each row of the perturbation dataframe 404 includes a single perturbation-level image embedding corresponding to a particular perturbation. The perturbation mapping system 106 can also generate a metadata dataframe 406 corresponding to the perturbation dataframe 404.

To generate the corresponding metadata dataframe 406, the perturbation mapping system 106 can aggregate metadata corresponding to the perturbation-level image embeddings to generate aggregated embedding metadata. The perturbation mapping system 106 can aggregate metadata in a variety of different ways. For example, in some implementations, the perturbation mapping system 106 aggregates metadata by merging metadata of individual phenomic digital images into a new merged metadata representation. To illustrate, for phenomic digital images captured on different dates, the perturbation mapping system 106 can merge the date information to a date range for the corresponding perturbation-level image embedding.

Rather than merging metadata, the perturbation mapping system 106 can also aggregate metadata by combining or joining metadata from individual assays. For example, the perturbation mapping system 106 can concatenate metadata or associate the metadata under a common perturbation-level identifier. In this manner, the perturbation mapping system 106 can associate all underlying metadata for individual phenomic digital images with a particular perturbation-level image embedding.

Further, the perturbation mapping system 106 can generate the metadata dataframe 406 such that each row of the metadata dataframe 406 includes the aggregated embedding metadata associated with the perturbation-level image embedding for each cell perturbation. Moreover, the perturbation mapping system 106 generates the dataframes such that the metadata dataframe 406 corresponds, row by row, to the perturbation dataframe 404. In some implementations, the perturbation mapping system 106 generates the metadata dataframe 406 to include an embedding identifier that maps to a corresponding embedding identifier of the metadata dataframe 406. The perturbation mapping system 106 can utilize the embedding identifier to align perturbation embeddings with corresponding metadata for rapid retrieval and analysis.

The perturbation mapping system 106 can also utilize the metadata in combination with perturbation image embeddings in responding to similarity queries from client devices. For example, the perturbation mapping system 106 can receive similarity queries that are limited to subsets of perturbation image embeddings. The perturbation mapping system 106 can utilize the metadata dataframe 406 to identify the pertinent subset of perturbation image embeddings (e.g., filter by date, well, cell type, etc.).

The perturbation mapping system 106 can also provide metadata from the metadata dataframe 406 in generating query responses. For example, the perturbation mapping system 106 can determine similarity measures for certain perturbation-level image embeddings and provide corresponding metadata to a client device. The client device can then display the corresponding metadata, such as when the underlying assays were conducted, the cell types utilized, the location of the experiments, etc. Thus, the perturbation mapping system 106 can cell image embeddings from the perturbation dataframe 404 and corresponding aggregated embedding metadata from the metadata dataframe 406 transmit a query response by transmitting the cell image embeddings and the aggregated embedding metadata to a client device.

As noted above, in some implementations, the perturbation mapping system 106 can regularly update the perturbation dataframe 404 and the metadata dataframe 406 with new cell image embeddings and their corresponding metadata as the perturbation mapping system 106 incorporates this new data into the database. For instance, the perturbation mapping system 106 can regenerate these dataframes regularly as the perturbation mapping system 106 incorporates additional experimental data (e.g., perturbation images) into the perturbation database 402. Indeed, as the perturbation mapping system 106 incorporates additional perturbation images from additional perturbation experiments, the perturbation mapping system 106 synthesizes the additional data by embedding the perturbation images and applying the various filtering, aligning, and aggregation models described above with respect to FIGS. 3A and 3B. The perturbation mapping system 106 can then regenerate each of the dataframes with the new perturbation-level image embeddings and corresponding metadata. Thus, in response to receiving additional cell image embeddings (from additional phenomic digital images), the perturbation mapping system 106 can generate updated cell image embeddings (by aligning and aggregating the additional cell image embeddings with previous/existing cell image embeddings). By generating the perturbation dataframe 404 and the corresponding metadata dataframe 406, the perturbation mapping system 106 facilitates accessing the cell image embeddings for generating a query response to a similarity query.

In some implementations, the perturbation mapping system 106 further includes a benchmarking database 408 for determining and providing additional relationship data (e.g., corresponding to a perturbation heatmap). Indeed, the perturbation mapping system 106 generates and maintains the benchmarking database 408 for storing verified relationship information (e.g., relationships between genes, compounds, and/or diseases). For instance, the perturbation mapping system 106 extracts relationships from external databases and identifies new relationships (e.g., based on the perturbation database). In some implementations, the perturbation mapping system 106 maintains the benchmarking database 408 as a stand-alone database. In some embodiments, the perturbation mapping system 106 maintains the benchmarking database as part of the perturbation database 402 and/or as part of the metadata dataframe 406. Moreover, the perturbation mapping system 106 can incorporate and analyze the data from the benchmarking database 408 with the perturbation heatmap when generating graphical user interfaces as will be described in further detail with regard to FIGS. 6A and 6B.

Figure 5:
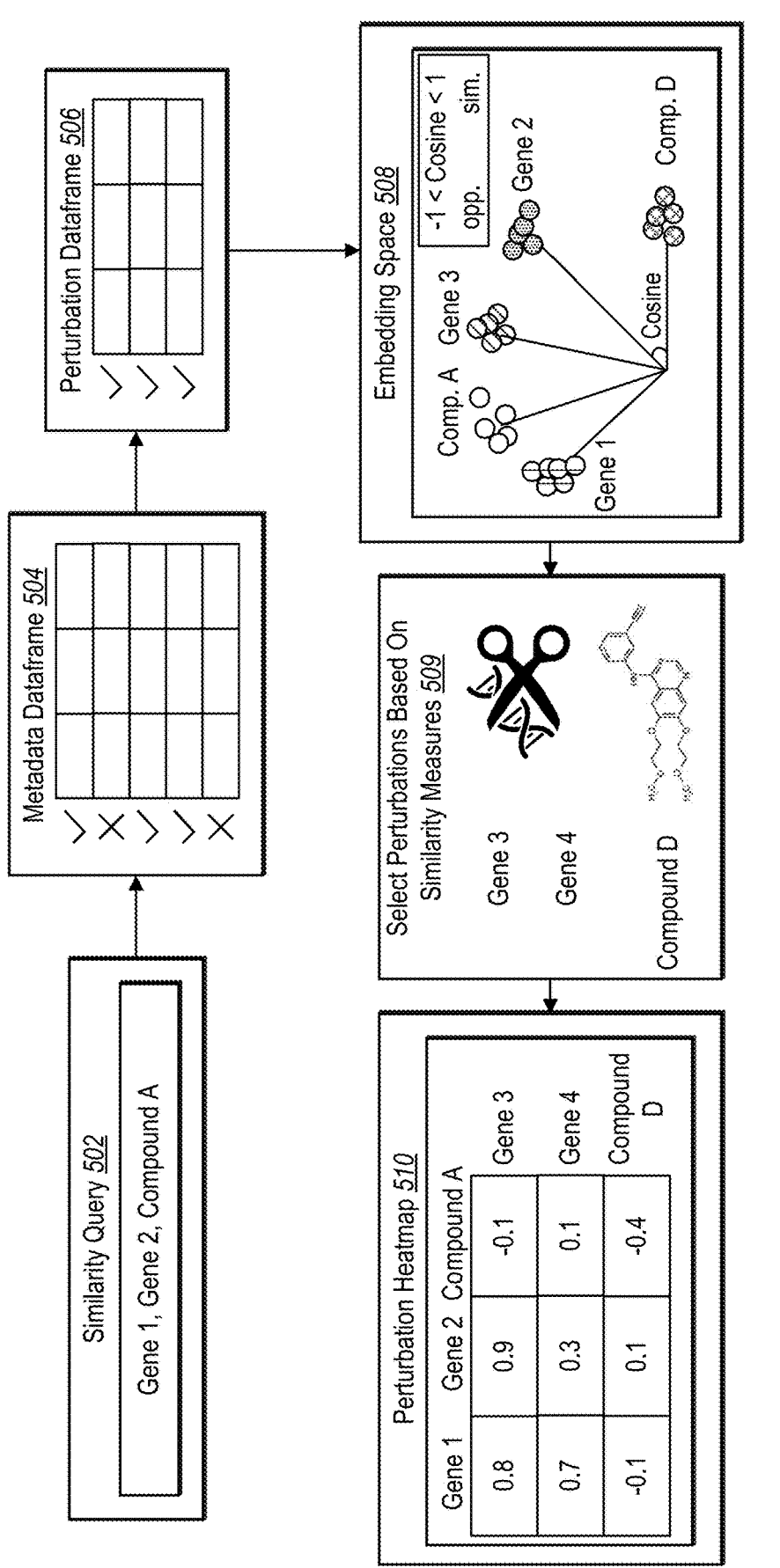
FIG. 5 illustrates determining a similarity measure between cell perturbations and generating a perturbation heatmap in response to the similarity query in accordance with one or more embodiments.

As mentioned above, in response to a similarity query 502, the perturbation mapping system 106 can generate a query response, for example by generating a perturbation heatmap 510 displaying similarity measures between perturbations. For instance, FIG. 5 illustrates determining a similarity measure between cell perturbations and generating the perturbation heatmap 510 in response to the similarity query 502 in accordance with one or more embodiments. Specifically, in response to the similarity query 502, the perturbation mapping system 106 can access the perturbation embeddings in a perturbation dataframe 506 via a metadata dataframe 504. Further, the perturbation mapping system 106 can determine a similarity measure between the queried perturbation embeddings and other perturbation embeddings in the database in an embedding space 508. The perturbation mapping system 106 performs an (optional) act 509 of selecting perturbations based on similarity measures. Moreover, the perturbation mapping system 106 can generate a query response, such as the perturbation heatmap 510 displaying the determined similarity measures (for the selected perturbations).

As noted previously, in response to the similarity query 502, the perturbation mapping system 106 can access the perturbation embeddings in the perturbation dataframe 506 via the metadata dataframe 504. For example, the perturbation mapping system 106 receives the similarity query 502 from a client device including one or more cell perturbations such as gene perturbation queries Gene 1 and Gene 2 and compound perturbation queries Compound A and Compound B as shown in FIG. 5. Further, the perturbation mapping system 106 can access the perturbation embeddings corresponding to these perturbation queries in the metadata dataframe 504. For instance, the perturbation mapping system 106 can identify the metadata dataframe 504 rows corresponding to the perturbations (e.g., the perturbation queries) of the similarity query 502. Further, the perturbation mapping system 106 can compare the perturbation embeddings of the perturbation dataframe 506 to the identified metadata in the rows of the metadata dataframe 504. Thus, the perturbation mapping system 106 can access the perturbation embeddings in the rows of the perturbation dataframe 506 corresponding to the identified rows of the metadata dataframe 504 as shown in FIG. 5.

As mentioned previously, in some implementations, the perturbation mapping system 106 utilizes the metadata dataframe 504 to identify the pertinent perturbation embeddings in the perturbation dataframe 506. For example, the perturbation mapping system 106 can receive a query that includes an identifier or feature of a gene or compound. The perturbation mapping system 106 can search for the identifier or feature in the metadata dataframe 504, determine the pertinent perturbation from the metadata dataframe, and then access the corresponding perturbation embedding from the perturbation dataframe 506.

Further, in some embodiments, the perturbation mapping system 106 can determine a similarity measure between perturbation embeddings corresponding to the queried perturbations and other perturbation embeddings in the database. For instance, in the embedding space 508, the perturbation mapping system 106 can determine a similarity measure, such as a cosine similarity or feature space distance measurement (e.g., Euclidean distance between feature vectors), between the queried perturbations (and/or the other perturbations of the database).

Indeed, FIG. 5 illustrates the perturbation mapping system 106 determining a cosine similarity between the perturbation embedding for queried perturbation Gene 1 and perturbation embeddings of other perturbations of the database (e.g., Gene 3 and Compound D). Moreover, the perturbation mapping system 106 can determine a similarity measure between the perturbation embedding for each of the queried perturbations and the other database perturbation embeddings to generate a query response (e.g., the perturbation heatmap 510) for display on a client device.

In some implementations, the perturbation mapping system 106 can compare perturbation embeddings for the queried perturbations (e.g., determine similarity measures between Gene 1 and Gene 2). In such embodiments, the perturbation mapping system 106 provides similarity measures for Gene 1 and Gene 2. In some implementations, the perturbation mapping system 106 compares perturbation embeddings for queried perturbations and additional perturbation embeddings from the database. In such circumstances, the perturbation mapping system 106 can also perform the act 509 of selecting perturbations based on these similarity measures.

For example, the perturbation mapping system 106 can compare the perturbation embedding for Gene 1 with a plurality of additional embeddings (for Gene 3, Gene, 4, Gene 5, Gene 6, Compound B, Compound C, and Compound D). The perturbation mapping system 106 can determine similarity measures based on each of these comparisons. Moreover, the perturbation mapping system 106 can select which perturbations to surface based on the similarity measures. For example, the perturbation mapping system 106 can select apply a threshold (e.g., a threshold number, a threshold percentage, or a threshold similarity score) and determine the perturbations that satisfy the threshold to select those to surface in a perturbation heatmap (e.g., the top 10, the top 10%, or those perturbations that satisfy a threshold similarity measure selected by a client device). In this manner, the perturbation mapping system 106 can identify those perturbations that are most relevant to the similarity query 502.

Thus, in one or more implementations, the perturbation mapping system 106 compares a first cell image embedding (for a first query perturbation) with a second cell image embedding (for a second query perturbation). In some implementations, the perturbation mapping system 106 cell image embeddings (for query perturbations) with additional cell image embeddings corresponding to additional cell perturbations.

As just mentioned, in some implementations, the perturbation mapping system 106 can generate a query response, such as the perturbation heatmap 510 displaying the determined similarity measures. Specifically, the perturbation mapping system 106 can transmit to the client device a query response including the determined similarity measures between the perturbation embeddings corresponding to cell perturbations of the similarity query 502. Indeed, the perturbation mapping system 106 can generate for display on a client device an interactive, two-dimensional perturbation heatmap 510 portraying the similarity measures, thereby displaying the identified perturbation relationships. As shown in FIG. 5 for example, the perturbation mapping system 106 can generate the perturbation heatmap 510 showing the similarity measures between the queried perturbations Gene 1, Gene 2, and Compound A and perturbations corresponding to the other embeddings of the perturbation database such as Gene 3, Gene 4, and Compound D (e.g., the perturbations satisfying the threshold), as shown in FIG. 5.

Although not illustrated, the perturbation mapping system 106 can iteratively perform the process shown in FIG. 5. For example, the perturbation mapping system 106 can iteratively receive similarity queries identify perturbation image embeddings and provide perturbation comparisons to client devices. Moreover, the perturbation mapping system 106 can update the metadata dataframe 504 and the perturbation dataframe 506 based on updated image embeddings and corresponding metadata. For instance, the perturbation mapping system 106 can receive, from an additional client device, an additional similarity query comprising an additional set of cell perturbations. Moreover, the perturbation mapping system 106 can access updated cell image embeddings corresponding to the additional set of cell perturbations. Further, the perturbation mapping system 106 can determine additional similarity measures for the additional set of cell perturbations from the updated cell image embeddings corresponding to the additional set of cell perturbations of the additional similarity query.

Figure 6A:
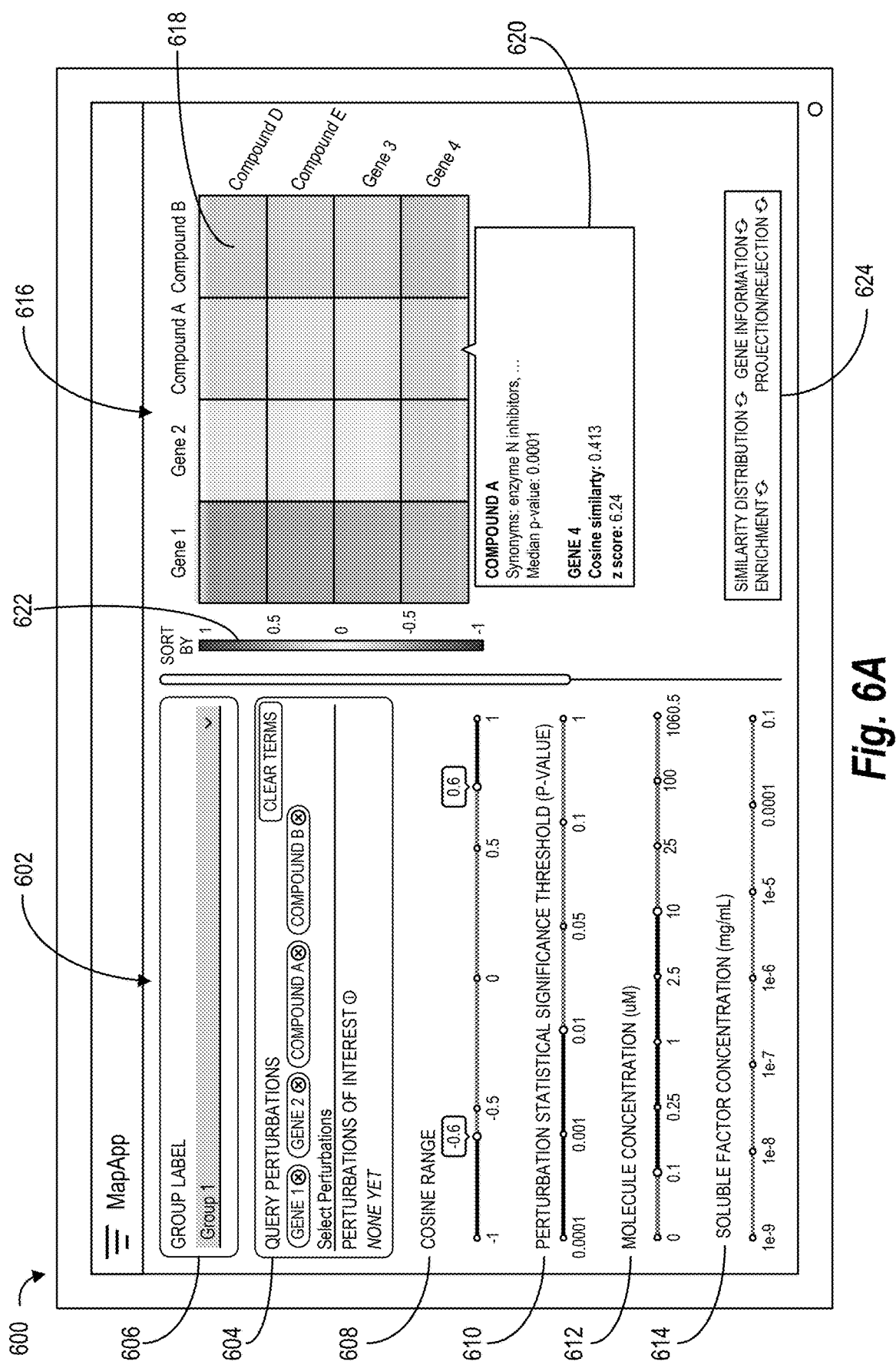
FIGS. 6A and 6B illustrate an exemplary graphical user interface for displaying an interactive perturbation heatmap of perturbation relationships in accordance with one or more embodiments.
Figure 6B:
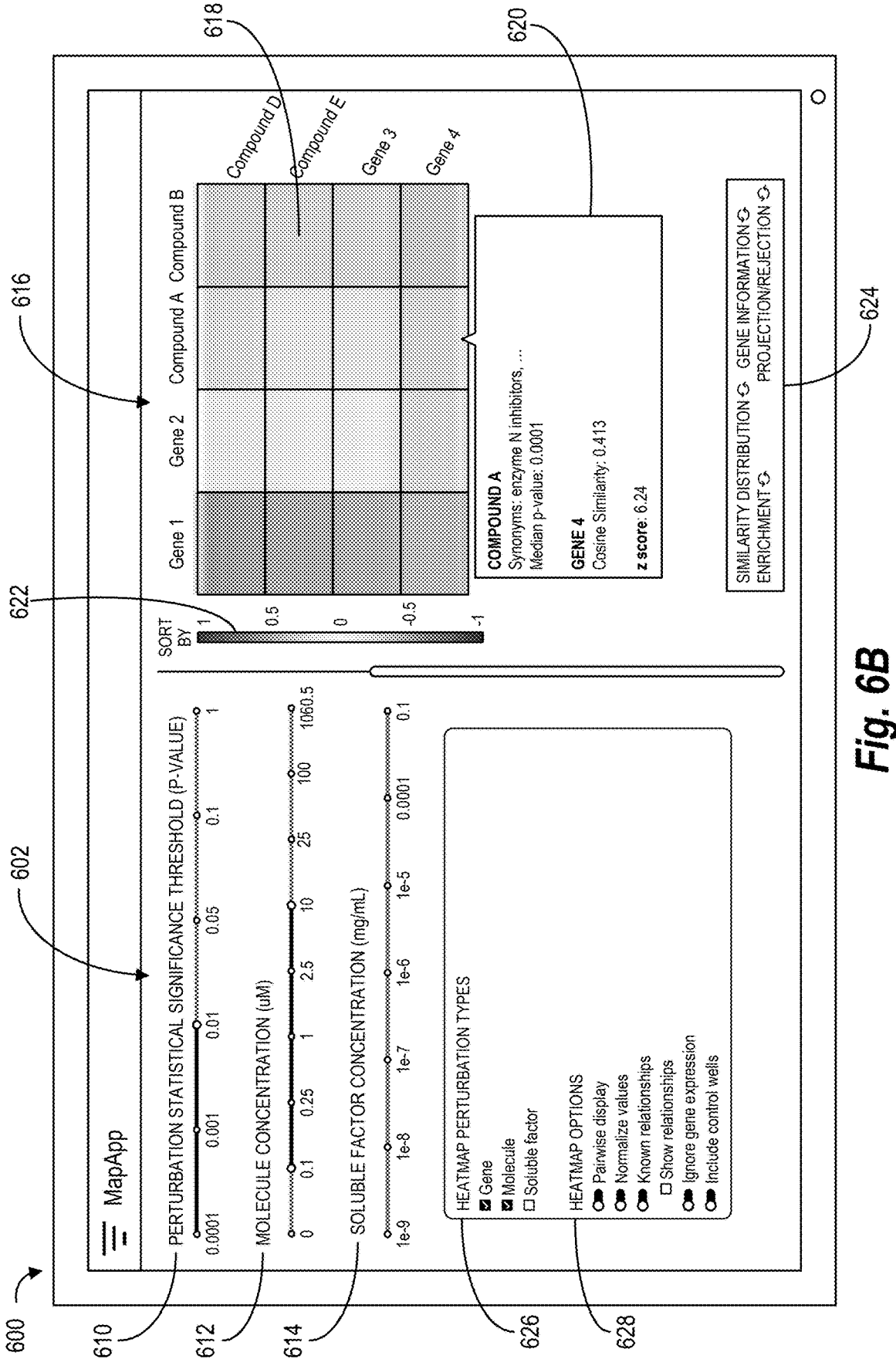

As just mentioned, in one or more embodiments, the perturbation mapping system 106 can generate a perturbation heatmap showing the similarity measure between queried perturbations and perturbations of the perturbation database. For example, FIGS. 6A and 6B illustrate an exemplary graphical user interface 600 on a client device displaying an interactive perturbation heatmap 618 of perturbation relationships in accordance with one or more embodiments. Indeed, FIG. 6A shows the exemplary graphical user interface 600 displaying the interactive perturbation heatmap 618 along with user interface elements for adjusting parameters of the perturbation heatmap 618 and user interface elements for displaying additional data for further analysis of the query response. Additionally, FIG. 6B illustrates the exemplary graphical user interface 600 displaying the interactive perturbation heatmap 618 along with additional user interface elements for adjusting parameters of the perturbation heatmap 618. Indeed, FIG. 6B illustrates the graphical user interface 600 wherein the perturbation mapping system 106 generates additional user interface elements in a left pane 602 of the graphical user interface 600 beneath the user interface elements of the left pane 602 shown in FIG. 6A. In some embodiments, for example, the perturbation mapping system 106 can generate the graphical user interface 600 to enable scrolling of the left pane 602 to display additional user interface elements. Indeed, the perturbation mapping system 106 can generate the graphical user interface 600 for display on a requestor device (e.g., a device requesting the similarity measure between queried perturbations and perturbations of the database).

As shown in FIG. 6A, the perturbation mapping system 106 generates the graphical user interface 600 for displaying the interactive perturbation heatmap 618 of queried perturbation relationships. Moreover, the perturbation mapping system 106 generates a right pane 616 and the left pane 602.

As mentioned above, in one or more embodiments, the perturbation mapping system 106 can generate user interface elements for receiving perturbation queries including, for example, the perturbation query element 604 as shown in FIG. 6A. Indeed, the perturbation mapping system 106 can receive a perturbation query via the perturbation query element 604 with one or more query perturbations such as gene perturbation queries Gene 1 and Gene 2 and compound perturbation queries Compound A and Compound B (as shown in the perturbation query element 604 of FIG. 6A). As used herein, a perturbation query element refers to a graphical user interface element for entering and/or receiving a perturbation query. For example, a perturbation query element can include a text element or a drop down element (populated with labeled genes or compounds corresponding to gene/compound queries). Thus, the perturbation mapping system 106 can provide perturbation query element 604 by providing a first plurality of selectable options for a plurality of gene knockout perturbations (e.g., a dropdown list of gene knockouts) and a second plurality of selectable options for a plurality of compound perturbations (e.g., a dropdown list of compounds). The perturbation mapping system 106 can determine different cell perturbations to query based on user interaction with these selectable options.

As described above, in response to receiving a perturbation query (e.g., a similarity query), the perturbation mapping system 106 can access perturbation image embeddings corresponding to the pertinent perturbations and compare the perturbation image embeddings and/or additional perturbation image embeddings. Specifically, the perturbation mapping system 106 determines similarity measures and generates a perturbation heatmap based on the similarity measures. For example, the perturbation mapping system 106 can identify a threshold similarity measure (selected by a client device) and surface those perturbations that satisfy the threshold similarity measures.

For example, FIG. 6A illustrates a similarity measure element 608 (e.g., for selecting a similarity measure, such as cosine similarity) in selecting perturbations for generating a perturbation heatmap. Indeed, the perturbation mapping system 106 can receive a similarity measure range via the similarity measure element 608 and apply the similarity measure to select perturbations in generating a perturbation heatmap. As illustrated in FIG. 6, the perturbation mapping system 106 utilizes cosine similarity threshold and a slider for selecting positive and negative thresholds (e.g., a similarity range). The perturbation mapping system 106 can utilize a variety of different similarity measures and graphical user interface elements (e.g., a text entry element, a drop down menu, a scroll bar, etc.).

As shown in FIG. 6A, the perturbation mapping system 106 can also generate and provide a significance threshold element 610. A significance threshold element allows for user selection of a significance threshold in generating a perturbation heatmap. For example, in, the perturbation mapping system 106 can determine a statistical significance corresponding to a particular embedding or set of embeddings. To illustrate, the perturbation mapping system 106 can determine a p-value (or probability value) indicating a likelihood of an observed data, signal, or relationship. Thus, a small p-value suggests that observed data is unlikely to have occurred by chance. For example, the perturbation mapping system 106 can determine a likelihood that a particular embedding, (or relationship) is indicative of an observed data signal rather than statistical chance. In particular, the perturbation mapping system 106 can analyze/compare data in the database to determine statistical probabilities that a perturbation embedding reflects random noise. The perturbation mapping system 106 can also generate or utilize other statistical significance thresholds or values (such as confidence intervals or Bayes factors).

The perturbation mapping system 106 can also apply a statistical significance threshold in generating a perturbation heatmap. For example, the perturbation mapping system 106 can surface or select those perturbations with a statistical significance that satisfies the threshold selected via the significance threshold element 610. Similarly, the perturbation mapping system 106 can exclude or filter those perturbations that fail to satisfy the selected threshold.

To illustrate, in one or more embodiments, the perturbation mapping system 106 determines a p-value for a particular embedding (e.g., a measure indicating a likelihood or confidence that a particular embedding reflects a meaningful data observation or signal rather than random noise). For example, consider a circumstance where a plurality of well-level embeddings are distributed across vastly different regions or directions within a feature space. In combining these well-level embeddings to a perturbation embedding, the perturbation mapping system 106 can determine a p-value for the perturbation embedding (e.g., a high p-value indicating a high confidence that the perturbation embedding reflects random noise). The perturbation mapping system 106 compares the p-value to the selected significance threshold (from the significance threshold element 610) and excludes or filters the embedding in generating the heatmap. Although the foregoing example describes filtering a perturbation-level embedding, the perturbation mapping system 106 can filter well-level embeddings or similarity measures from the heatmap based on a p-value and p-value threshold.

Additionally, the perturbation mapping system 106 can also generate and provide a molecule concentration element 612 and/or a soluble concentration element 614 (e.g., compound concentration elements for selecting perturbations to include in a perturbation heatmap). As discussed above, compound perturbation experiments can include molecules and/or soluble factors applied to cells at different concentrations. Based on interaction with the molecule concentration element 612 and/or a soluble concentration element 614 the perturbation mapping system 106 can select perturbations for a perturbation heatmap that correspond to the selected concentrations. Indeed, the perturbation mapping system 106 can generate and/or retrieve perturbation image embeddings based only on perturbation images corresponding to the selected concentrations. The perturbation mapping system 106 can then generate similarity measures for those particular concentration-specific perturbation embeddings and include those concentration-specific similarity measures.

Moreover, in one or more implementations, the perturbation mapping system 106 can further restrict the returned perturbations based on receiving a group label via the group label element 606 (e.g., Group 1 as shown in FIG. 6A). In particular, perturbation embeddings can be grouped together based on the attributes of the perturbations as indicated in the metadata of the embeddings. For example, the perturbation mapping system 106 can group the perturbations based on a variety of factors including, by way of example and not limitation, the cell type perturbed in the perturbation experiments, the particular models used in generating the perturbation-level image embeddings, the particular flow of models used in generating the perturbation-level image embeddings, or other attributes/features of the perturbation experiments and/or the models used in generating the embeddings of the database. Thus, the perturbation mapping system 106 can restrict the returned perturbations to perturbations associated with the group label received as part of the query response.

Although FIG. 6A illustrates various elements portrayed as sliders (or other element types), the perturbation mapping system 106 can utilize a variety of graphical user interface elements. For instance, the perturbation mapping system 106 can utilize text elements, scroll wheel elements, drop down elements, or radio buttons for the various elements portrayed in FIG. 6A.

As shown in FIG. 6A, based on user interaction with the various elements 604-614, the perturbation mapping system 106 can generate and provide the perturbation heatmap 618 for display via the graphical user interface 600. Specifically, the perturbation mapping system 106 searches a metadata dataframe to identify those perturbation image embeddings that satisfy pertinent criteria (e.g., concentration, group label, perturbation identifier). Moreover, the perturbation mapping system 106 can extract corresponding perturbation image embeddings and generate similarity measures. The perturbation mapping system 106 can then surface those perturbations that satisfy the parameters/criteria selected via the various elements 604-614.

Specifically, the perturbation mapping system 106 can compare the perturbation image embeddings for the query perturbations to determine similarity measures. The perturbation mapping system 106 can also compare the perturbation image embeddings with additional perturbation image embeddings for other perturbations to determine additional similarity measures. The perturbation mapping system 106 then selects those perturbations that satisfy the user-selected (or otherwise defined) criteria.

As shown, the perturbation mapping system 106 can utilize the query perturbations to generate columns of the perturbation heatmap 618 as part of the query response. Moreover, the perturbation mapping system 106 generates the rows of the perturbation heatmap 618 with the selected perturbations identified in response to the similarity query (i.e., the returned perturbations) as part of the query response. Specifically, Compound D, Compound E, Gene 3, and Gene 4 satisfy the similarity threshold, statistical significance threshold, and other pertinent criteria selected. Indeed, as illustrated in FIGS. 6A and 6B, the perturbation mapping system 106 generates the perturbation heatmap 618 displaying the similarity measures between the query perturbations (e.g., Gene 1, Gene 2, Compound A, and Compound B shown as the column names of the perturbation heatmap 618) and the returned perturbations (e.g., Compound D, Compound E, Gene 3, and Gene 4 shown as the row names of the perturbation heatmap 618).

Further, in one or more embodiments, the perturbation mapping system 106 can generate the perturbation heatmap 618 with a visual indication of the similarity measures. For example, in one or more implementations, the perturbation mapping system 106 can generate the perturbation heatmap 618 to include variable shading corresponding to differing similarity measure values. For example, the perturbation mapping system 106 can generate darker shading to correspond to a high similarity measure value (e.g., cosine similarity values close to 1) representing pheno-similar perturbations or corresponding to a low similarity measure value (e.g., cosine similarity values close to −1) representing pheno-opposite perturbations. In some embodiments, the perturbation mapping system 106 can generate similarity values with a color scale, for example a color scale including multiple different colors with variable shading. For instance, the perturbation mapping system 106 can generate a color scale including red and blue shading. In these or other embodiments, dark red shading can indicate a high similarity measure value (e.g., cosine similarity values close to 1)

representing pheno-similar perturbations and dark blue shading can indicate a low similarity measure value (e.g., cosine similarity values close to −1) representing pheno-opposite perturbations.

Moreover, in some implementations, the perturbation mapping system 106 can generate the heatmap key 622 for inclusion in the graphical user interface 600. Indeed, the heatmap key 622 can display the differing shading of the heatmap, including for example, the colors and shading of the perturbation heatmap 618 with a color scale and shading as shown in FIGS. 6A and 6B. For example, the heatmap key 622 of FIGS. 6A and 6B can show differing similarity measure values (e.g., 1, 0.5, 0, −0.5, and −1) alongside the corresponding color and shading. Indeed, the heatmap key can display the darkest red shading at the top of the heatmap key 622 alongside the number 1, lighter shading adjacent to the number 0.5, no shading adjacent to the number 0, light blue shading adjacent to −0.5, and the darkest blue shading adjacent to the number −1. Thus, the perturbation mapping system 106 can provide a visual key to the visual indication of the similarity measures.

Additionally, in one or more embodiments, the perturbation mapping system 106 can generate the perturbation data element 620 in response to a user interaction with a similarity measure portrayed in the perturbation heatmap 618. As used herein, a perturbation data element refers to a graphical user interface element for displaying information regarding two perturbations. In particular, a perturbation data element includes am element that appears, generates, or populates in response to selection of a similarity measure (or other representation of two perturbations). Thus, a perturbation data element can include an overlay element or pop-up element that appears in response to user interaction (e.g., a click or hover) over a cell of a perturbation heatmap.

For example, as illustrated, the perturbation mapping system 106 provides additional information (e.g., features regarding cell perturbations) for display via the perturbation data element 620. As used herein, features regarding cell perturbations refers to characteristics or information regarding cell perturbations (e.g., gene perturbations and/or compound perturbations). Specifically, in response to detecting user interaction with a cell of the perturbation heatmap 618 corresponding to Compound A and Gene 4, the perturbation mapping system 106 provides the perturbation data element 620 and populates the perturbation data element 620 with features corresponding to Compound A and Gene 4. As discussed previously, the perturbation mapping system 106 can access or generate these features. For instance, the perturbation mapping system 106 can access some features from a metadata dataframe comprising metadata corresponding to individual perturbations. Moreover, the perturbation mapping system 106 can generate certain features (e.g., similarity scores based on perturbation image embeddings or p-values based on statistical distributions).

Specifically, the perturbation mapping system 106 can populate a perturbation data element 620 with features by including the selected perturbations (e.g., the gene names or the compound IDs and synonyms), the statistical significance of each perturbation (e.g., the p-value), the similarity value (e.g., the cosine similarity), known relationships (extracted from the relationship database), and a z score for the relationship. For example, as shown in FIG. 6A, in response to a user interaction with the similarity measure between Compound A and Gene 4, the perturbation mapping system 106 generates the perturbation data element 620 with the two perturbations (i.e., Compound A and Gene 4), the synonyms of Compound A, the median p-value, and the cosine similarity.

Additionally, in one or more embodiments, the perturbation mapping system 106 can populate the perturbation data element 620 with information genes and/or compounds generated by one or more language machine learning models (e.g., large language models). For example, the perturbation mapping system 106 can generate digital text prompts based on anchor genes and/or anchor compounds (indicating potential biological relationships). For instance, the perturbation mapping system 106 can generate digital text prompts with rating instructions and/or contextual information instructions. The perturbation mapping system 106 can utilize the digital text prompts with a language machine learning model to generate rating metrics and/or contextual information regarding potential biological relationships. In one or more implementations, the perturbation mapping system 106 provides these rating metrics and/or contextual information for display via the perturbation data element 620. For example, the perturbation mapping system 106 can identify rating metrics or contextual information to display as described in UTILIZING BIOLOGICAL MACHINE LEARNING REPRSENTATIONS AND A LANGUAGE MACHINE LEARNING MODEL FOR INITIATING COMPOUND EXPLORATION PROGRAMS, U.S. application Ser. No. 18/521,910, filed Nov. 28, 2023, the contents of which are incorporated by reference herein in their entirety.

Thus, in one or more implementations the perturbation mapping system 106 identifies a perturbation relationship via the perturbation heatmap 618. Further, the perturbation mapping system 106 generates and passes one or more prompts containing the perturbation relationship information to a large language model to generate a rating metric, program rating, and/or contextual information. Moreover, the perturbation mapping system 106 populates the perturbation data element 620 with the rating metric, program rating, and/or contextual information for a given perturbation in response to a user interaction with a similarity measure portrayed in the perturbation heatmap 618 as described above.

Moreover, the perturbation mapping system 106 can generate the perturbation data element 620 in a variety of forms. For example, in some implementations, the perturbation mapping system 106 generates the perturbation data element as a heatmap overlay element. As used herein, a heatmap overlay element refers to a graphical user interface element that overlays (or covers) a portion of a heatmap. For example, a heatmap overlay can include a pop-up box that appears over a portion of a heatmap in response to selection of a cell within the heatmap. Thus, as shown, the perturbation data element 620 partially overlaps the perturbation heatmap 618 as a heatmap overlay element. In some implementations, the perturbation data element 620 is a different element (e.g., a text box element that does not overlay the perturbation heatmap 618).

Furthermore, in one or more implementations, the perturbation mapping system 106 can generate the graphical user interface 600 to include the data analysis menu element 624 including one or more elements for further data analysis. For example, in these or other embodiments, the perturbation mapping system 106 can generate the data analysis menu element 624 in the right pane 616. Indeed, the data analysis menu element 624 can include further data analysis elements, for example, a similarity distribution element, a gene information element, an enrichment element, and/or a projection/rejection element as shown in FIGS. 6A and 6B. These data analysis elements will be discussed in further detail with regard to FIGS. 7-10.

As mentioned above, in one or more implementations, the perturbation mapping system 106 can generate additional user interface elements for selecting/adjusting parameters of the perturbation heatmap 618. For example, FIG. 6B illustrates a perturbation type selection element 626 and a heatmap options elements 628. The perturbation mapping system 106 can utilize input received from the perturbation type selection element 626 to generate or modify the perturbation types included in the perturbation heatmap 618. For example, the perturbation mapping system 106 can select or filter one or more of gene perturbations, molecule perturbations, or soluble factor perturbations in response to the input received via the perturbation type selection element 626. To illustrate, the perturbation mapping system 106 can only surface gene perturbations (and withhold other perturbations) in the perturbation heatmap 618 in response to selection of a gene perturbation type via the perturbation type selection element 626.

In some embodiments, the perturbation mapping system 106 can further generate or modify the perturbation heatmap 618 in response to input received via the heatmap options elements 628. For example, the perturbation mapping system 106 can display pairwise (N by N) relationships for a given set of N perturbations. Specifically, upon selection of pairwise display, the perturbation mapping system 106 can limit the perturbation heatmap 618 to a comparison of the query perturbations identified via the perturbation query element 604 (i.e., without identifying additional perturbations). Upon deselection of pairwise display, the perturbation mapping system 106 can identify additional perturbations that satisfy the selected parameters/criteria.

Moreover, the perturbation mapping system 106 can normalize the similarity measures of the query response shown in the perturbation heatmap 618 in response to receiving input via the normalize values element. Indeed, in one or more implementations, by default the perturbation mapping system 106 returns similarity measures (e.g., raw cosine values) in the query response. However, in response to receiving input via the normalize values element, the perturbation mapping system 106 can redistribute the cosine values for the selected perturbations from –1 to 1 (e.g., to make differentiations more visible/clear). Further, in response to this input, the perturbation mapping system 106 can display the normalized cosine values and the percentile rank in the perturbation data element 620 in response to an interaction with a similarity measure portrayed in the perturbation heatmap 618.

Further, in response to a user interaction with the known relationships element, the perturbation mapping system 106 can filter perturbations based on known relationships and/or display known relationship information (e.g., gene-gene, gene-compound, or compound-compound relationships) from a benchmark database. Indeed, the perturbation mapping system 106 can generate and maintain a database of verified relationships. For instance, the perturbation mapping system 106 can extract relationships from external databases as well as identify new relationships (e.g., based on the perturbation database).

In some implementations, the perturbation mapping system 106 filters known or unknown relationships from the perturbations in generating the perturbation heatmap 618 (based on user interactions with the known relationship element). In some implementations, the perturbation mapping system 106 shows or hides these known relationships.

For example, the perturbation mapping system 106 includes the perturbations in the perturbation heatmap 618, searches the database, and provides a known indicator for display for known relationships (and/or an unknown indicator for unknown relationships).

For instance, in some implementations, known relationships will appear at the bottom of a tooltip menu when hovering over a relationship (including information about how the two perturbations affect each other, the source, type of relationship and sign). To illustrate, the perturbation mapping system 106 can utilize the following notation:

Entity 1-Entity 2 means Entity 1 and Entity 2 have a known relationship

Entity 1>Entity 2 means Entity 1 affects Entity 2

Entity 1< >Entity 2 means Entity 1 and Entity 2 are in a protein complex.

Moreover, a positive sign can indicate a positive/promoting effect and a negative sign can indicate a negative/inhibitor effect. If there is no relationship information in the database in some implementations no known relationship information will appear.

As shown in FIG. 6B, the perturbation mapping system 106 can also include a gene expression element. In some implementations, the perturbation mapping system 106 will filter perturbations based on a measure of gene expression. For instance, the perturbation mapping system 106 can remove perturbations based on a z-score calculated for fragments per kilobase of transcript per million mapped reads (zFPKM). Interacting with the gene expression element can remove this filter (thereby including genes only based on the p-value filter). In some implementations, the perturbation mapping system 106 can filter the query response to include only genes having a specified zFPKM value (e.g., a zFPKM value of –3 or greater).

Furthermore, in some embodiments, the perturbation mapping system 106 can further modify the perturbation heatmap 618 in response to user interaction the control wells element. As mentioned previously, in some implementations, the perturbation mapping system 106 includes control wells in batch perturbation experiments to apply alignment models. Based on interactions with the control wells element, the perturbation mapping system 106 can include (or exclude) perturbation image embeddings for control wells in generating the perturbation heatmap 618.

Although not illustrated, in some implementations, the perturbation mapping system 106 also includes a split by experiment element. Based on interaction with a split by experiment element, the perturbation mapping system 106 can return/provide experiment level data for the query. In particular, the perturbation mapping system 106 can generate experiment-level similarity measures (e.g., from experiment level image embeddings generated from aggregating embeddings at the experiment level). For instance, the perturbation mapping system 106 can include experiment name now next to all the perturbations labels on the columns and rows and in an overlay element. Moreover, the perturbation mapping system 106 can generate an overlay element that includes the p-values on a per experiment basis. This view allows for easy identification of consistency of a perturbation or set of relationships between individual experiment replicates.

Figure 7:
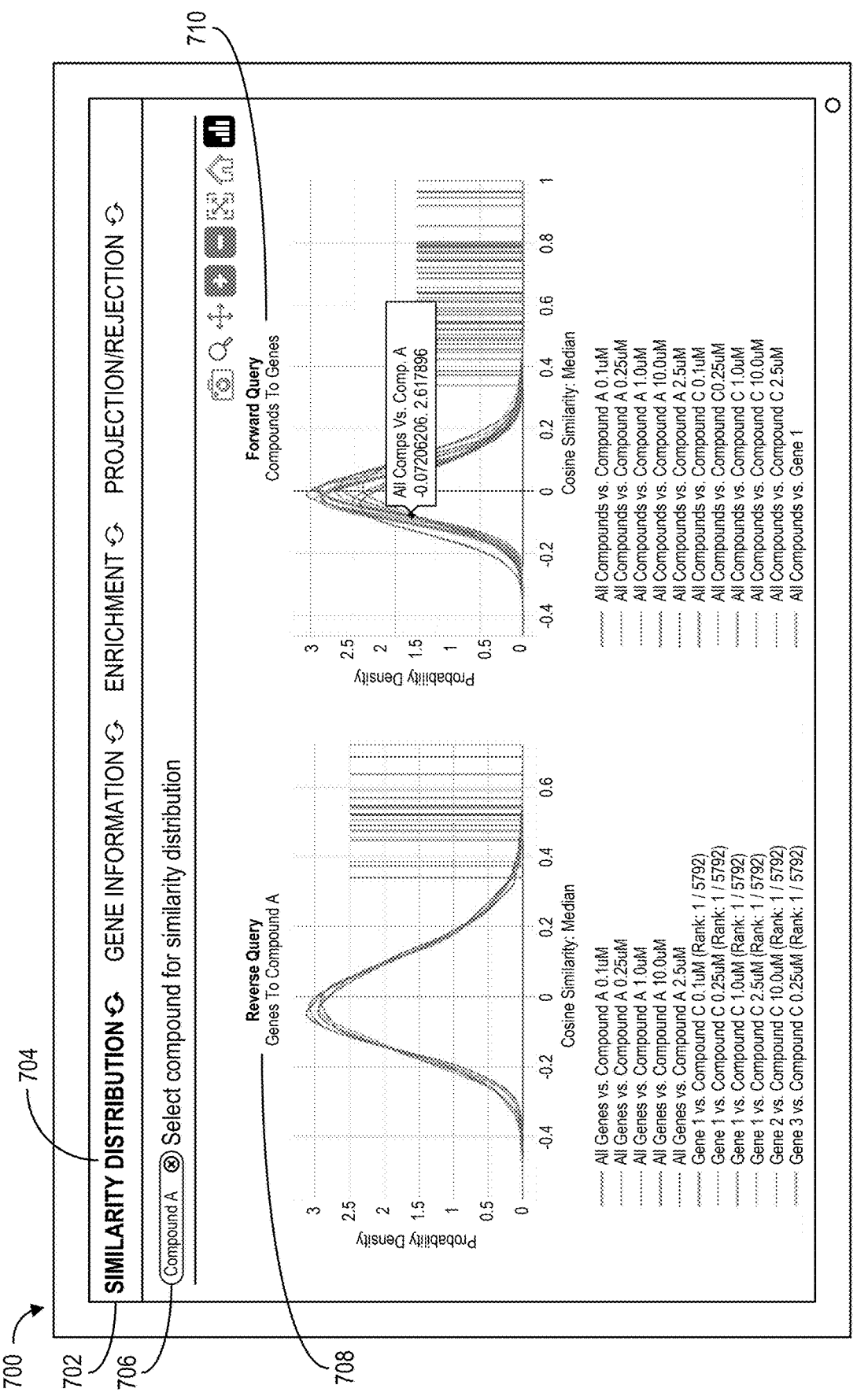
FIG. 7 illustrates an exemplary graphical user interface for displaying similarity distribution data of a query response in accordance with one or more embodiments.

As mentioned above, in some embodiments, the perturbation mapping system 106 can generate a graphical user interface to include a data analysis menu element (e.g., the data analysis menu element 624) including one or more elements for further data analysis (e.g., a similarity distribution element, a gene information element, an enrichment element, and/or a projection/rejection element). Indeed, FIGS. 7-10 illustrate these various additional user interface elements and data (e.g., upon selection of elements from the data analysis menu element 624 of FIG. 6). For example, FIG. 7 illustrates an exemplary graphical user interface 700 for displaying similarity distribution data for a query response in accordance with one or more embodiments.

In particular, the perturbation mapping system 106 can generate the graphical user interface 700 to include a data analysis menu element 702 (including a similarity distribution element 704, a gene information element, an enrichment element, and a projection/rejection element), a perturbation selection element 706, and similarity distribution data (e.g., reverse query results 708 and forward query results 710). Indeed, the perturbation mapping system 106 can generate the similarity distribution data and additional user interface elements for display via the user interface of the requestor device in response to a user interaction with the similarity distribution element 704.

As used herein, the term similarity distribution element refers to a graphical user interface element that includes similarity distributions (e.g., graphs or statistical information regarding a probability distribution of similarity measures). For example, the user interface 700 provides similarity distribution information that allows client devices to determine statistical measures related to the similarity measures illustrated in a perturbation heatmap. For example, upon selection of a particular cell of a perturbation heatmap, the perturbation mapping system 106 can generate the user interface 700 include similarity distribution information corresponding to a particular relationship or relationships (e.g., gene-compound or other relationship). Thus, the perturbation mapping system 106 analyzes the underlying embeddings/representations of each perturbation and performs a statistical analysis to determine the likelihood of a similarity measure as compared to a null distribution in high dimensional space.

Further, in some implementations, the perturbation mapping system 106 can generate the similarity distribution data in response to receiving a perturbation selection via the perturbation selection element 706. Specifically, the perturbation mapping system 106 can receive a perturbation selection comprising a returned perturbation (e.g., Compound A as shown in FIG. 7) to generate for display in the graphical user interface 700 the reverse query results 708 and the forward query results 710 for the selected returned perturbation.

Indeed, the perturbation mapping system 106 can generate the reverse query results 708 to display the distributions of similarity values of the query perturbations relative to the selected perturbation. In particular, the reverse query results 708 illustrate distributions of similarity measures (e.g., cosine similarity) relative to probability density for compound gene combinations. Specifically, the perturbation mapping system 106 performs a statistical analysis of similarity measures, determines the probability of particular similarity measures across different combinations, and plots the distribution. Thus, FIG. 7 illustrates curves for all genes relative to Compound A (at different concentrations) and individual genes relative to a different compound (Compound C). This provides insight into the impact or variability of similarity measures across genes (and whether the compound at particular concentrations is having a unique impact relative to other combinations).

Similarly, the perturbation mapping system 106 can generate the forward query results 710 to display the distributions similarity measures for different compound-compound combinations. Specifically, the perturbation mapping system 106 performs a statistical analysis of similarity measures, determines the probability of particular similarity measures across different compound-compound combinations, and plots the distribution. Thus, the forward query results 710 illustrate distributions for all compounds relative to Compound A (at different concentrations) and all compounds relative to an additional compound (Compound C). This provides insight into the impact or of similarity measures across compounds.

As mentioned above, in one or more embodiments, the perturbation mapping system 106 can generate gene information data for a query response and additional user interface elements in response to receiving an indication of a user interaction with a gene information element 804. As used herein, the term gene information element refers to a graphical user interface element that includes contextual information, characteristics, or features regarding one or more genes. For instance, a gene information element can include a table populated with details regarding a gene. Thus, as a client device identifies potential genes of interest, the perturbation mapping system 106 can extract and identify gene information (e.g., from a gene database) and surface the gene information via the client device.

Figure 8:
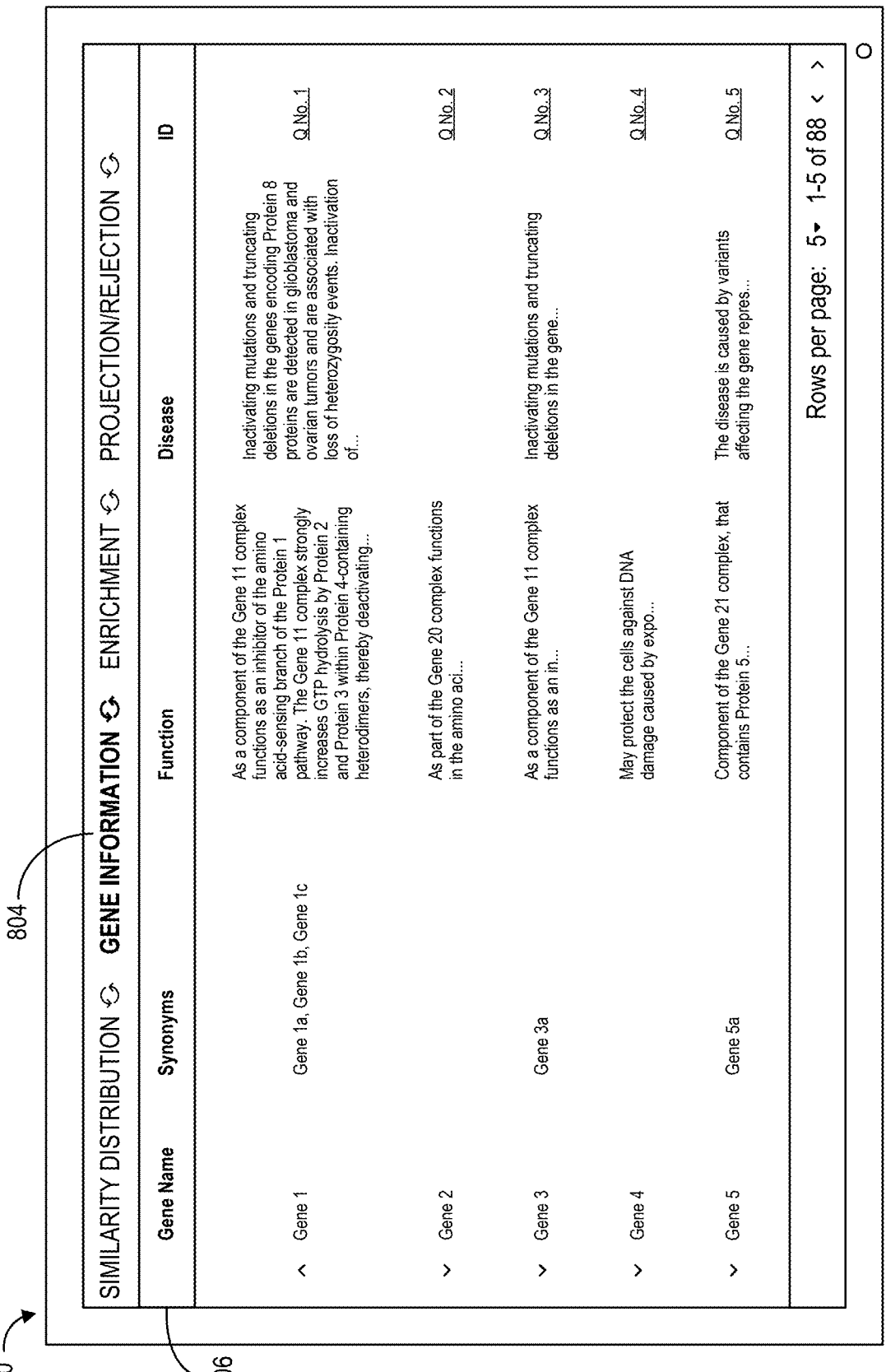
FIG. 8 illustrates an exemplary graphical user interface for displaying gene information data of a query response in accordance with one or more embodiments.

For example, FIG. 8 illustrates an exemplary graphical user interface 800 for displaying gene information data of a query response in accordance with one or more embodiments. Specifically, the perturbation mapping system 106 can generate the graphical user interface 800 in response to selection of the gene information element 804. The user interface 800 includes a gene information header element 806 (including headers such as a gene name header, a synonyms header, a function header, a disease header, and an ID header). Indeed, the perturbation mapping system 106 can generate the gene information data and the gene information header element 806 in response to a user interaction with the gene information element 804.

The perturbation mapping system 106 generates gene information illustrated in the user interface 800 based on genes portrayed in a perturbation heatmap. Thus, for example, the perturbation mapping system 106 can identify perturbations to include in a perturbation heatmap and then provide gene information corresponding to those genes (e.g., upon selection of gene information from the data analysis menu element 624).

As illustrated, the perturbation mapping system 106 can generate gene information of the returned gene perturbations of a query response in a table format. For example, the perturbation mapping system 106 can generate the gene information data to correspond to headers of the gene information header element 806. Indeed, the perturbation mapping system 106 can generate the gene information display to include, by way of example, and not limitation, the gene names, gene name synonyms, known functions of the gene name, diseases associated with the gene, and an identification number (ID) corresponding to the genes. Further, the perturbation mapping system 106 can extract the gene information from publicly available external locations (e.g., the UniPro database).

Figure 9:
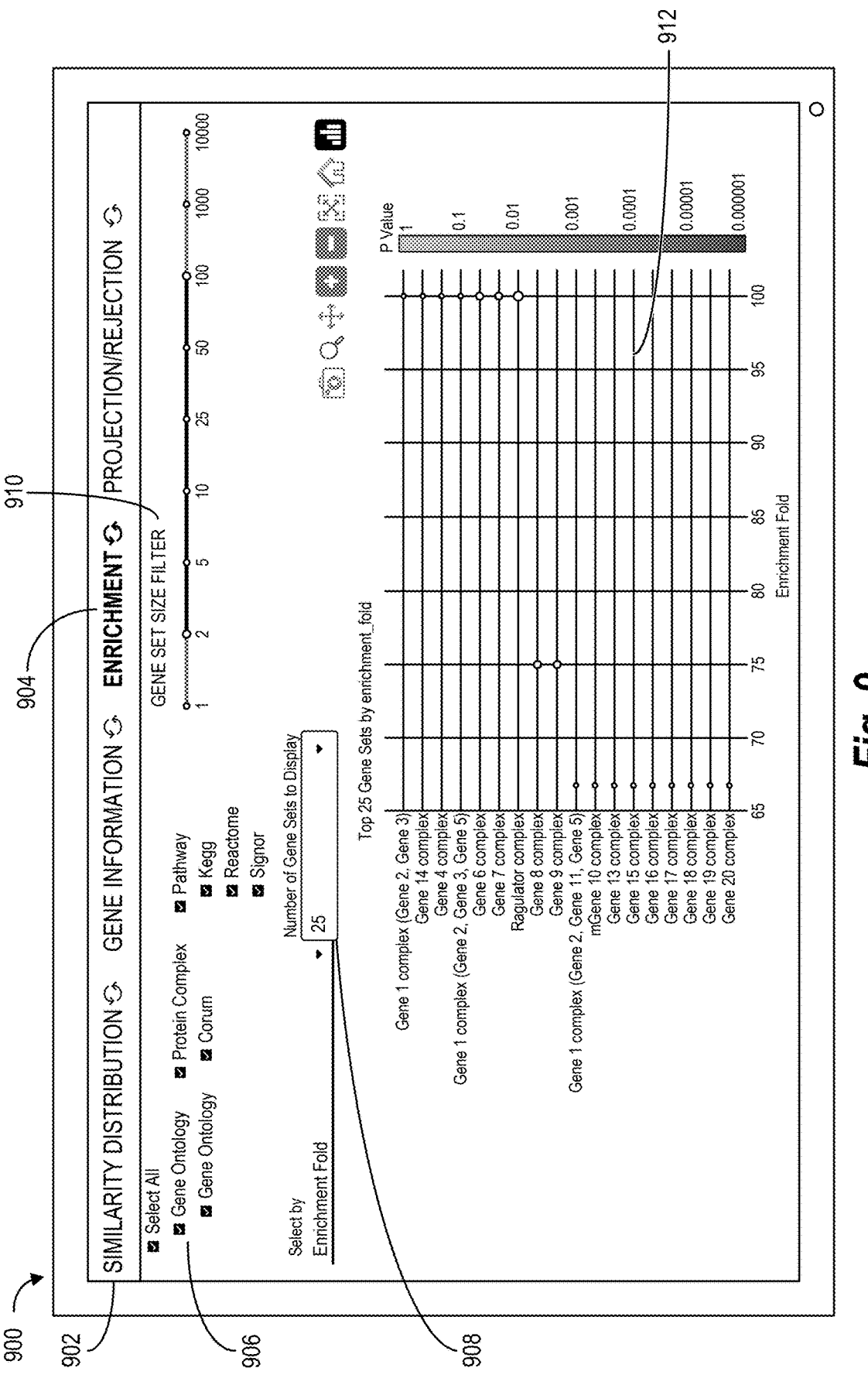
FIG. 9 illustrates an exemplary graphical user interface for displaying gene enrichment data of a query response in accordance with one or more embodiments.

As mentioned previously, the perturbation mapping system 106 can generate gene enrichment data for a query response in response to receiving an indication of a user interaction with an enrichment element. For example, FIG. 9 illustrates an exemplary graphical user interface 900 for displaying gene enrichment data 912 of a query response in accordance with one or more embodiments. In particular, the perturbation mapping system 106 can generate the graphical user interface 900 to include a data analysis menu element 902 (including a similarity distribution element, a gene information element, an enrichment element 904, and a projection/rejection element), a gene set element 906, a display element 908, a gene set size filter element 910 and the gene enrichment data 912. Indeed, the perturbation mapping system 106 can generate the gene enrichment data 912 and additional user interface elements for display via the user interface of the requestor device in response to a user interaction with the enrichment element 904.

As used herein, the term enrichment element refers to a graphical user interface for providing a gene set enrichment analysis. Gene set enrichment analysis refers to a computational and statistical method to identify and quantify representation of biological functions within a set of genes of interest. For example, a gene set enrichment analysis can perform statistical tests to determine whether certain biological terms or pathways over overrepresented in an input gene set compared to what would be expected by change. The perturbation mapping system 106 can utilize a variety of statistical tests for this purpose, including hypergeometric tests, Fisher's exact tests, and chi-squared tests. Thus, the perturbation mapping system 106 can generate an enrichment score and p-value for biological terms or pathways. Thus, an enrichment element includes a graphical user interface element that is operable to display information regarding these analysis, such as enrichment scores, p-values, or illustrations of statistical enrichment tests. The term enrichment element also includes interactive elements for modifying parameters for a gene set enrichment analysis. Thus, user interface 900 of FIG. 9 illustrates a gene set enrichment analysis in response to selection of the enrichment element 904.

In particular, in one or more implementations, the perturbation mapping system 106 can generate the gene enrichment data 912 for the genes of the returned gene perturbations in the query response based on various parameters. For example, the perturbation mapping system 106 can generate the gene enrichment data 912 of the genes corresponding to the returned gene perturbations in the form of a gene enrichment plot as illustrated in FIG. 9. This plot illustrates p-values of different gene sets corresponding to particular enrichment folds.

Further, the perturbation mapping system 106 can generate the gene enrichment data 912 to conform to various parameters. Moreover, the perturbation mapping system 106 can receive the various parameters such as a gene set, a gene set size, and display requirements in response to user interaction with the gene set element 906, the gene set size filter element 910, and the display element 908 respectively. For instance, in some embodiments, the perturbation mapping system 106 can generate the gene enrichment data 912 based on receiving a gene set such as one or more of a gene ontology set, a protein complex set, a CORUM set, and/or a pathway set. Additionally, the perturbation mapping system 106 can receive one or more pathways (e.g., KEGG, Reactome, SIGNOR) as part of the pathway set via the gene set element 906. Furthermore, the perturbation mapping system 106 can restrict the results of the gene enrichment data 912 by size of the gene set based on receiving a gene set size indication via the gene set size filter element 910.

Moreover, the perturbation mapping system 106 can organize the gene enrichment data 912 based on receiving display information via the display element 908. For example, the perturbation mapping system 106 can receive display information such as how to arrange the data in the gene enrichment plot (e.g., by enrichment fold, alphabetically, etc.) and the number of sets to display in the plot. By way of example, and not limitation, the perturbation mapping system 106 can generate the gene enrichment data 912 to display in a gene enrichment plot showing the top 25 gene sets by enrichment fold as shown in FIG. 9.

Further, in some embodiments, the perturbation mapping system 106 can generate a gene enrichment table (not shown) in addition to the gene enrichment plot. For example, the perturbation mapping system 106 can generate a gene enrichment table beneath the gene enrichment plot including information such as the Group (i.e., the gene set), the enrichment fold, the enrichment p-value, the specific genes of the set shown in the perturbation heatmap, and other relevant information known to a person having ordinary skill in the art.

Figure 10:
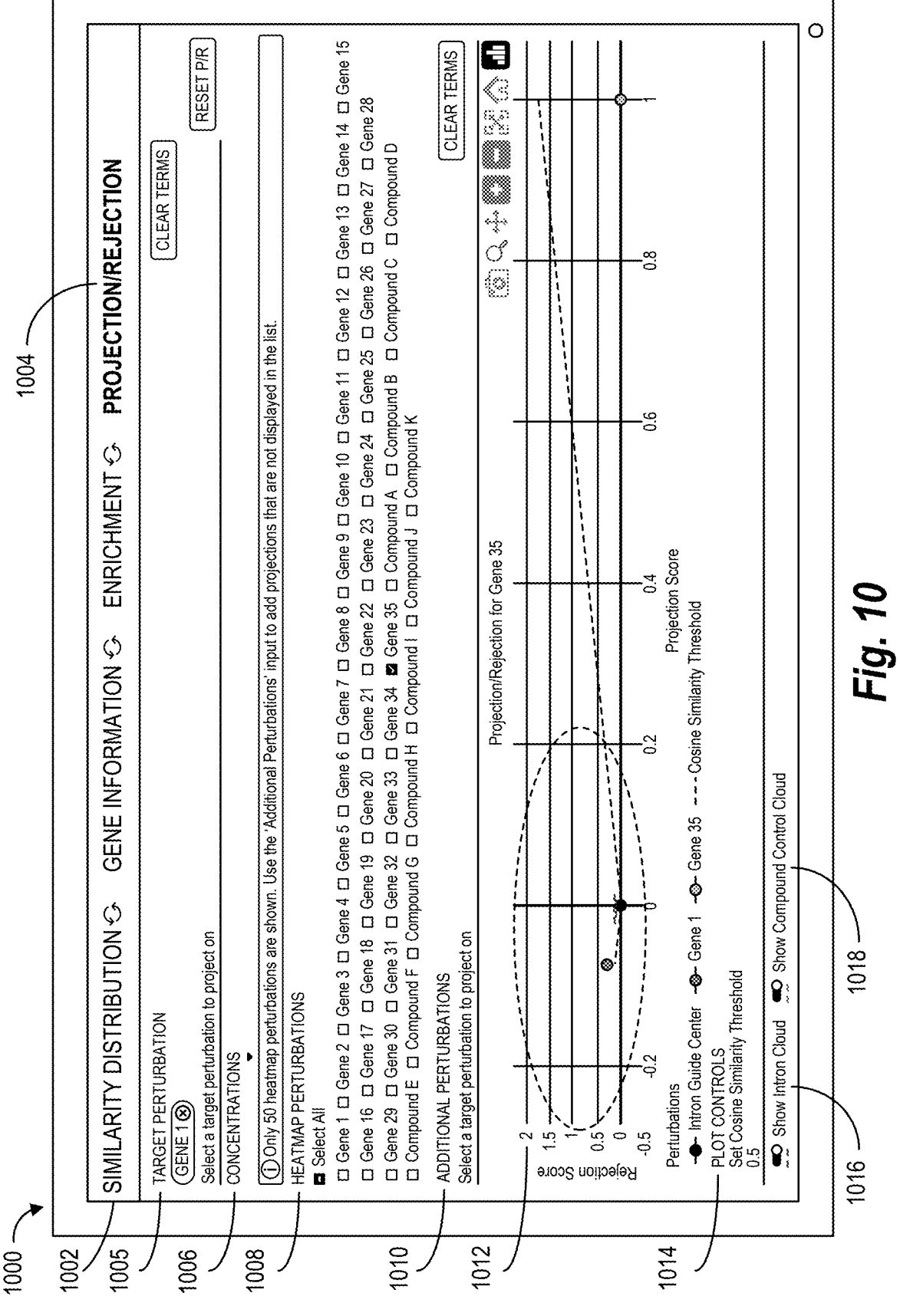
FIG. 10 illustrates an exemplary graphical user interface for displaying projection/rejection data of a query response in accordance with one or more embodiments.

As noted above, the perturbation mapping system 106 can generate projection/rejection data for a query response and additional user interface elements in response to receiving an indication of a user interaction with a projection/rejection element. For example, FIG. 10 illustrates an exemplary graphical user interface 1000 for displaying projection/rejection data 1012 of a query response in accordance with one or more embodiments. Specifically, the perturbation mapping system 106 can generate the graphical user interface 1000 to include a data analysis menu element 1002 including a similarity distribution element, a gene information element, an enrichment element, and a projection/rejection element 1004, as well as the projection/rejection data 1012, and additional user interface elements such as a target perturbation element 1005, a concentrations element 1006, a heatmap perturbations element 1008, an additional perturbations element 1010, a plot controls element 1014, a show intron cloud element 1016, and a show compound control cloud element 1018. Indeed, the perturbation mapping system 106 can generate the projection/rejection data and the additional user interface elements for display via the user interface of the requestor device in response to a user interaction with the projection/rejection element 1004.

As used herein, the term projection/rejection element refers to a graphical user interface element for displaying a direction and magnitude comparison of perturbations in high-dimensional feature space. In particular, a projection/rejection element includes an interface element that portrays a location of a reference embedding and a direction and magnitude of other embeddings relative to the reference embedding. Thus, a projection/rejection element can include a visual portrayal of a target embedding and other embeddings and a direction and distance magnitude between the embeddings within the feature space. In some implementations, the perturbation mapping system 106 projects perturbations onto a target perturbation and determines a magnitude and direction of other heatmap perturbations (e.g., relative to the target perturbation).

Further, in one or more embodiments, the perturbation mapping system 106 can generate the projection/rejection data 1012 for one or more returned perturbations in the query response with respect to a target perturbation according to one or more parameters received by the perturbation mapping system 106. Indeed, the perturbation mapping system 106 can receive a target perturbation (e.g., Gene 1 as shown in FIG. 10) via the target perturbation element 1005 and one or more returned perturbations (e.g., Gene 35 as shown in FIG. 10) via the heatmap perturbations element 1008. Moreover, the perturbation mapping system 106 can generate the projection/rejection data 1012 to display a projection/rejection for more than a single perturbation by receiving additional perturbations via a user interaction with the heatmap perturbations element 1008. Indeed, the perturbation mapping system 106 can include up to a threshold number of perturbations from the query response (e.g., 50 perturbations) for display in the heatmap perturbations element 1008. Further, the perturbation mapping system 106 can include, in the generated projection/rejection data 1012, perturbations from the query response not included for display in the heatmap perturbations element 1008. For instance, the perturbation mapping system 106 can receive these perturbations in response to user interaction with the additional perturbations element 1010. Furthermore, the perturbation mapping system 106 can generate the heatmap perturbations element 1008 to include only compound perturbations conforming to a specified concentration or concentration range via the concentrations element 1006.

Additionally, in one or more implementations, the perturbation mapping system 106 can generate the projection/rejection data 1012 based on receiving user interaction with the plot controls element 1014, the show intron cloud element 1016, and the show compound control cloud element 1018. For example, the perturbation mapping system 106 can generate the projection/rejection data 1012 with a specified cosine similarity threshold based on receiving a user interaction with the plot controls element 1014. Further, the perturbation mapping system 106 can show (or stop showing) an intron cloud graphic in the projection/rejection data 1012 in response to a user interaction with the show intron cloud element 1016. Similarly, the perturbation mapping system 106 can show (or stop showing) a compound control cloud graphic in the projection/rejection data 1012 based on receiving a user interaction with the show compound control cloud element 1018.

Further, the perturbation mapping system 106 can generate and provide the projection/rejection data 1012 to provide a visual representation of the magnitude and direction of a perturbation relative to a target perturbation. For example, the perturbation mapping system 106 can utilize the target perturbation received via the target perturbation element 1005 to generate a direction and magnitude for one or more perturbations of the heatmap received via the heatmap perturbations element 1008. Further, the perturbation mapping system 106 can provide the direction and magnitude for display in the graphical user interface 1000 (e.g., by showing a vector or points indicating the relative direction and magnitude). In this manner, the perturbation mapping system 106 can provide for display in the graphical user interface 1000 a representation of the magnitude and direction of the one or more perturbations of the heatmap relative to the target perturbation.

Although FIGS. 6A-10 illustrate a particular arrangement of user interface elements and features, the perturbation mapping system 106 can generate a user interface with a different arrangement or order of elements. For example, the perturbation mapping system 106 can utilize different panes (e.g., swap the left pane 602 and the right pane 616) or no panes. Similarly, the perturbation mapping system 106 can provide similarity distributions, gene information, enrichment information, or projection/rejection information directly in the user interface 600 (e.g., under the perturbation heatmap or in a different field or pane).

With regard to FIGS. 6A-10, it will be appreciated that a client can navigate across different illustrated elements through a single user interface (e.g., as part of a unified workflow). Thus, the perturbation mapping system 106 can detect user interactions with the elements 604-614 and/or the elements 626, 628 to dynamically modify the perturbation heatmap 618. Moreover, the perturbation mapping system

106 can dynamically modify similarity distributions, gene information, enrichment information, and projection/rejection information based on the different queries and query responses and illustrate similarity distributions, gene information, enrichment information, and projection/rejection information (e.g., based on user interaction with the data analysis menu element 624).

Indeed, the perturbation mapping system 106 can generate a modified perturbation heatmap based on user interaction with the elements 606-614 and/or 6026-628. To illustrate, in response to user interaction with a perturbation statistical significance threshold element or a compound concentration element, the perturbation mapping system 106 can provide an updated perturbation heatmap portraying similarity measures between a plurality of perturbation embeddings for the plurality of cell perturbations according to the statistical significance threshold or the compound concentration. Similarly, in response to user input of an updated similarity threshold via the similarity threshold element, the perturbation mapping system 106 can providing an updated perturbation heatmap portraying similarity measures for perturbations according to the updated similarity threshold.

Thus, the perturbation mapping system 106 can generate modified perturbation heatmaps and supporting data through a dynamic user interface to iteratively explore relationships between genes and compounds. This allows client devices to efficiently explore different relationships through minimal user interactions with the user interface 600. For instance, consider the following example use case.

Based on existing knowledge, a client is aware that Gene X encodes a scaffolding protein (Protein Y) that has emerged as a key regulator of integrin activation, which leads to actin remodeling, cell migration and adhesion. While integrins are promising targets for therapeutic intervention, including in fibrosis, targeting integrins themselves has had mixed success. Given Protein Y's implication in fibrosis and evidence that reduction of Protein Y activity could attenuate fibrosis in a number of models, targeting Protein Y may be a new therapeutic target to treat liver and other fibrotic indications. It has proven difficult to develop small molecule inhibitors using traditional biochemical approaches; however, the perturbation mapping system 106 can identify additional relationships in an accurate and efficient manner.

For example, a client device first seeks to perform a check to confirm the biological relationship. If the perturbation database indicates clear relationships between Gene X and other known interactor genes this provides additional confidence that the representation of the morphological effect of the loss of Gene X worth using to find novel relationships.

To identify relationships confirming gene relationships, a client device can toggle off the 'Compound' Perturbation Type (from the perturbation type selection element 626) to only display gene knockout results. The client device then enters a query (by entering Gene X into the perturbation query field 604). This results in a perturbation graph that illustrates strong phenosimilar relationships between Gene X and three other genes: Gene A, Gene B, and Gene C, all of which are in the Integrin signaling pathway.

Toggling on pairwise display (via the heatmap options elements 628) and adding these three genes to the perturbation query field 604 generates a modified perturbation heatmap illustrating strong clustering (all four gene knockouts have high similarity measures). The client device also enters additional genes that are farther downstream. A further modified perturbation heatmap confirms that these result in weaker relationships.

With these biological signals confirmed, the client continues with exploration of small molecules that show phenosimilarity to Gene X and its neighbors (Gene A, Gene B, and Gene C). The client device turns off pairwise display (via the heatmap options elements 628), changes the perturbation type selection to only compound (via the perturbation type selection element 626), removes the other selected perturbations, and (via the similarity measure element 608) moves the pheno-opposite normalized cosine range slider to −1 (to avoid looking for pheno-opposites) and relaxes the phenosimilar normalized cosine range slider to +0.57.

This results in a perturbation heatmap with dozens of small molecules (at various concentrations) meeting the +0.57 Normalized Cosine Range threshold for positive phenosimilarity to at least one of these four query genes. In particular, a small molecule, Compound Y, has nearly perfect phenosimilarity to Gene X at 10 uM. The client device chooses to inspect the level of selectivity of this compound to these four query genes by selecting the compound to obtain similarity distributions and scores for each gene (e.g., via the similarity distribution element 704). The resulting similarity distribution plot illustrates that Compound A begins to show highly selective relationships to these four query genes a 1 uM concentrations or higher.

Returning to the heatmap plot, the client device can see many NCE compounds with high similarity to Gene X, and choose to examine Compound Z, which shows strong similarity to Gene X and Gene A at 3 uM, but weaker similarity to Gene C. Examining the distribution plots for this compound (via the similarity distribution element 704) reveals how selective this molecule appears to be for these targets of interest. The client can examine the clustering of this compound with the 4 targets across all concentrations, by toggling on Pairwise Display (via the heatmap options elements 628), selecting the Gene Perturbation Type (via the perturbation type selection element 626), and adding Compound Z to the Query Perturbations Input (via the perturbation query field 604). This generates another modified perturbation heatmap that illustrates strong self-clustering of Compound Z (indicating stability across several concentrations), and clear similarities with Gene X and Gene A.

From here, the client can investigate and select additional compounds of interest as well as structural analogs to these small molecules and prioritize these for further analysis. As illustrated by the foregoing example, via the user interface 600 the perturbation mapping system 106 allows client devices to perform real-time comparisons and analysis of machine learning embeddings for different perturbations to accurately identify relationships between genes and compounds. Such an analysis with conventional systems would have required extensive queries, multiple user interfaces, hundreds and thousands of user interactions, and yielded less accurate information.

FIGS. 1-10, the corresponding text, and the examples provide a number of different systems, methods, and non-transitory computer readable media for embedding perturbation data via a machine learning model and filtering, aligning, and aggregating the embeddings to generate a genome-wide perturbation database. In addition to the foregoing, embodiments can also be described in terms of flowcharts comprising acts for accomplishing a particular result. For example, FIG. 11 illustrates a flowchart of an example sequence of acts in accordance with one or more embodiments.

While FIG. 11 illustrates acts according to some embodiments, alternative embodiments may omit, add to, reorder, and/or modify any of the acts shown in FIG. 11. The acts of FIG. 11 can be performed as part of a method. Alternatively, a non-transitory computer readable medium can comprise instructions, that when executed by one or more processors, cause a computing device to perform the acts of FIG. 11. In still further embodiments, a system can perform the acts of FIG. 11. Additionally, the acts described herein may be repeated or performed in parallel with one another or in parallel with different instances of the same or other similar acts.

FIG. 11 illustrates an example series of acts 1100 for embedding perturbation data via a machine learning model and filtering, aligning, and aggregating the embeddings to generate a genome-wide perturbation database. The series of acts 1100 can include an act 1102 of receiving a plurality of perturbation images portraying cells from a plurality of wells corresponding to a plurality of cell perturbations; an act 1104 of generating a plurality of well-level image embeddings from the plurality of perturbation images; an act 1106 of aligning the well-level image embeddings to generate aligned well-level image embeddings; an act 1108 of aggregating the well-level image embeddings to generate perturbation-level image embeddings; and an act 1110 of generating perturbation comparisons utilizing the perturbation-level image embeddings.

For example, in one or more embodiments, the series of acts 1100 can include receiving, from a client device, a similarity query comprising a plurality of cell perturbations; in response to receiving the similarity query, accessing cell image embeddings corresponding to the plurality of cell perturbations; determining similarity measures for the plurality of cell perturbations from the cell image embeddings corresponding to the plurality of cell perturbations of the similarity query; and transmitting, to the client device, a query response comprising the similarity measures from the cell image embeddings.

In one or more implementations, accessing the cell image embeddings corresponding to the plurality of cell perturbations further comprises: identifying a plurality of initial cell image embeddings; aggregating the plurality of initial cell image embeddings according to cell perturbations to generate the cell image embeddings; and generating a first dataframe comprising the cell image embeddings corresponding to the plurality of cell perturbations.

Moreover, in some embodiments, the series of acts 1100 can include aggregating metadata corresponding to the plurality of initial cell image embeddings to generate aggregated embedding metadata; generating a second dataframe comprising the aggregated embedding metadata of the cell image embeddings of the first dataframe; accessing the cell image embeddings from the first dataframe and corresponding aggregated embedding metadata from the second dataframe; and transmitting the query response by transmitting the cell image embeddings and the aggregated embedding metadata to the client device.

In addition, in some implementations, determining the similarity measures for the plurality of cell perturbations from the cell image embeddings comprises at least one of: comparing a first cell image embedding of the cell image embeddings with a second cell image embedding of the cell image embeddings; or comparing the cell image embeddings corresponding to the plurality of cell perturbations of the similarity query with additional cell image embeddings corresponding to additional cell perturbations.

Furthermore, in some embodiments, the series of acts 1100 can include receiving additional cell image embeddings; and aggregating the additional cell image embeddings and the plurality of initial cell image embeddings to generate updated cell image embeddings.

In some implementations, the series of acts 1100 can include receiving, from an additional client device, an additional similarity query comprising an additional set of cell perturbations; accessing the updated cell image embeddings corresponding to the additional set of cell perturbations; and determining additional similarity measures for the additional set of cell perturbations from the updated cell image embeddings corresponding to the additional set of cell perturbations of the additional similarity query.

Moreover, in some embodiments, determining the similarity measures between the plurality of cell perturbations by comparing the cell image embeddings corresponding to the plurality of cell perturbations of the similarity query comprises determining a cosine similarity between the cell image embeddings corresponding to the plurality of cell perturbations of the similarity query.

In addition, in some implementations, receiving, from the client device, the similarity query comprising the plurality of cell perturbations comprises receiving at least one of a gene perturbation query or a compound perturbation query.

Furthermore, in some embodiments, transmitting, to the client device, the query response comprising the similarity measures comprises transmitting, to the client device, a perturbation heatmap portraying the similarity measures.

FIGS. 1-10, the corresponding text, and the examples provide a number of different systems, methods, and non-transitory computer readable media for determining a similarity measure between cell perturbation embeddings in response to a similarity query and generating a query response for display on a client device. In addition to the foregoing, embodiments can also be described in terms of flowcharts comprising acts for accomplishing a particular result. For example, FIG. 12 illustrates a flowchart of an example sequence of acts in accordance with one or more embodiments.

While FIG. 12 illustrates acts according to some embodiments, alternative embodiments may omit, add to, reorder, and/or modify any of the acts shown in FIG. 12. The acts of FIG. 12 can be performed as part of a method. Alternatively, a non-transitory computer readable medium can comprise instructions, that when executed by one or more processors, cause a computing device to perform the acts of FIG. 12. In still further embodiments, a system can perform the acts of FIG. 12. Additionally, the acts described herein may be repeated or performed in parallel with one another or in parallel with different instances of the same or other similar acts.

FIG. 12 illustrates an example series of acts 1200 for determining a similarity measure between cell perturbation embeddings in response to a similarity query and generating a query response for display on a client device. The series of acts 1200 can include an act 1202 of receiving a similarity query comprising a plurality of cell perturbations; an act 1204 of accessing cell image embeddings corresponding to the plurality of cell perturbations; an act 1206 of determining a similarity measure between the plurality of cell perturbations by comparing the cell image embeddings corresponding to the plurality of cell perturbations of the similarity query; and an act 1208 of transmitting a query response comprising the similarity measure between the plurality of cell perturbations of the similarity query.

For example, in one or more embodiments, the series of acts 1200 can include receiving a plurality of perturbation images portraying cells from a plurality of wells corresponding to a plurality of cell perturbations; generating, utilizing a machine learning model, a plurality of well-level image embeddings from the plurality of perturbation images; aligning, utilizing an alignment model, the plurality of well-level image embeddings to generate aligned well-level image embeddings; aggregating, according to perturbations of one or more perturbation experiments, the aligned well-level image embeddings to generate perturbation-level image embeddings; and generating perturbation comparisons utilizing the perturbation-level image embeddings.

In one or more implementations, receiving the plurality of perturbation images comprises: receiving a first perturbation image portraying a first cell resulting from at least one of: a first gene knockout perturbation of a first gene or a first compound perturbation; and receiving a second perturbation image portraying a second cell resulting from at least one of: a second gene knockout perturbation of a second gene or a second compound perturbation.

Additionally, in one or more embodiments, the series of acts 1200 can include determining statistical significance values for the perturbation-level image embeddings; and filtering one or more of the perturbation-level image embeddings having a statistical significance value below a statistical significance threshold.

Moreover, in some embodiments, generating, utilizing the machine learning model, the plurality of well-level image embeddings comprises: generating, utilizing a convolutional neural network, a first well-level embedding for the first perturbation image; and generating, utilizing the convolutional neural network, a second well-level embedding for the second perturbation image.

In addition, in some implementations, the plurality of perturbation images comprise a plurality of patch images portraying portions of wells from the plurality of wells and wherein generating the plurality of well-level image embeddings comprises: generating, utilizing the machine learning model, a plurality of patch-level embeddings from the plurality of perturbation images; and aggregating the plurality of patch-level embeddings according to the plurality of wells to generate the plurality of well-level image embeddings.

Furthermore, in some embodiments, the series of acts 1200 can include receiving an additional plurality of perturbation images portraying additional cells; generating, utilizing the machine learning model, an additional plurality of well-level image embeddings; and generating modified perturbation-level image embeddings from the additional plurality of well-level image embeddings and the plurality of well-level image embeddings.

In some implementations, the series of acts 1200 can include filtering the plurality of well-level image embeddings according to one or more quality criterion.

Moreover, in some embodiments, aligning, utilizing the alignment model, the plurality of well-level image embeddings to generate the aligned well-level image embeddings comprises aligning a set of well-level image embeddings from a plurality of different perturbation experiments having a shared perturbation according to a statistical aligning model.

In addition, in some implementations, the series of acts 1200 can include generating, utilizing a proximity bias model, proximity bias corrected perturbation-level image embeddings; and generating the perturbation comparisons from the proximity bias corrected perturbation-level image embeddings.

Furthermore, in some embodiments, generating the perturbation comparisons utilizing the perturbation-level image embeddings comprises: determining similarity measures between the perturbation-level image embeddings; generating a perturbation heatmap comprising the similarity measures for the plurality of cell perturbations; and providing the perturbation heatmap for display via a client device.

FIGS. 1-10, the corresponding text, and the examples provide a number of different systems, methods, and non-transitory computer readable media for generating graphical user interfaces for display of perturbation heatmaps on a requestor device. In addition to the foregoing, embodiments can also be described in terms of flowcharts comprising acts for accomplishing a particular result. For example, FIG. 13 illustrates a flowchart of an example sequence of acts in accordance with one or more embodiments.

While FIG. 13 illustrates acts according to some embodiments, alternative embodiments may omit, add to, reorder, and/or modify any of the acts shown in FIG. 13. The acts of FIG. 13 can be performed as part of a method. Alternatively, a non-transitory computer readable medium can comprise instructions, that when executed by one or more processors, cause a computing device to perform the acts of FIG. 13. In still further embodiments, a system can perform the acts of FIG. 13. Additionally, the acts described herein may be repeated or performed in parallel with one another or in parallel with different instances of the same or other similar acts.

FIG. 13 illustrates an example series of acts 1300 for generating graphical user interfaces for display of perturbation heatmaps on a requestor device. The series of acts 1300 can include an act 1302 of providing a perturbation query element for selection of a plurality of cell perturbations; an act 1304 of providing a perturbation heatmap portraying similarity measures from a plurality of perturbation embeddings for the plurality of cell perturbations; and an act 1306 of providing a perturbation data element comprising one or more features of the plurality of cell perturbations corresponding to the similarity measure.

For example, in one or more embodiments, the series of acts 1300 can include providing, for display via a user interface of a requestor device, a perturbation query element for selection of a plurality of cell perturbations; in response to user interaction with the perturbation query element, providing, for display via the user interface of the requestor device, a perturbation heatmap portraying similarity measures between a plurality of perturbation embeddings for the plurality of cell perturbations; in response to user interaction with a similarity measure portrayed via the perturbation heatmap, providing, for display on the requestor device, a perturbation data element comprising one or more features of the plurality of cell perturbations corresponding to the similarity measure.

In one or more implementations, providing the perturbation query element comprises providing, for display via the user interface, a first plurality of selectable options for a plurality of gene knockout perturbations and a second plurality of selectable options for a plurality of compound perturbations, and further comprising determining the plurality of cell perturbations for the perturbation heatmap based on one or more user interactions with the first plurality of selectable options or the second plurality of selectable options.

Moreover, in some embodiments, the series of acts 1300 can include determining the similarity measure of the similarity measures by: determining a first perturbation image embedding for a first perturbation of the plurality of cell perturbations; determining a second perturbation image embedding for a second perturbation; and comparing the first perturbation image embedding and the second perturbation image embedding to determine the similarity measure.

In addition, in some implementations, providing the perturbation heatmap comprises providing, for display via the user interface of the requestor device, the similarity measure in a cell within a row of the perturbation heatmap corresponding to the first perturbation and within a column of the perturbation heatmap corresponding to the second perturbation.

Furthermore, in some embodiments, providing the perturbation data element comprises, providing, for display via the user interface of the requestor device based on the user interaction with the similarity measure, a heatmap overlay element portraying a first set of features corresponding to the first perturbation and a second set of features corresponding to the second perturbation.

In some implementations, the series of acts 1300 can include providing, for display via the user interface of the requestor device, a similarity measure element for selection of a similarity threshold; determining that the similarity measure between the first perturbation image embedding and the second perturbation image embedding satisfies the similarity threshold; and based on the similarity measure satisfying the similarity threshold, selecting the second perturbation to include within the perturbation heatmap.

Moreover, in some embodiments, the series of acts 1300 can include providing, for display via the user interface of the requestor device, at least one of a perturbation statistical significance threshold element for selection of a statistical significance threshold or the molecule concentration element 612 for selection of a compound concentration; and in response to user interaction with the perturbation statistical significance threshold element or the molecule concentration element 612, providing, for display via the user interface of the requestor device, an updated perturbation heatmap portraying similarity measures between a plurality of perturbation embeddings for the plurality of cell perturbations according to the statistical significance threshold or the compound concentration.

In addition, in some implementations, the series of acts 1300 can include providing, for display with the perturbation heatmap via the user interface of the requestor device, at least one of: a similarity distribution element for displaying similarity distributions, a gene information element for displaying gene information, or an enrichment element for displaying gene set enrichment analysis.

Embodiments of the present disclosure may comprise or utilize a special purpose or general-purpose computer including computer hardware, such as, for example, one or more processors and system memory, as discussed in greater detail below. Implementations within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, implementations of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some implementations, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multiprocessor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Implementations of the present disclosure can also be implemented in cloud computing environments. In this description, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 14:
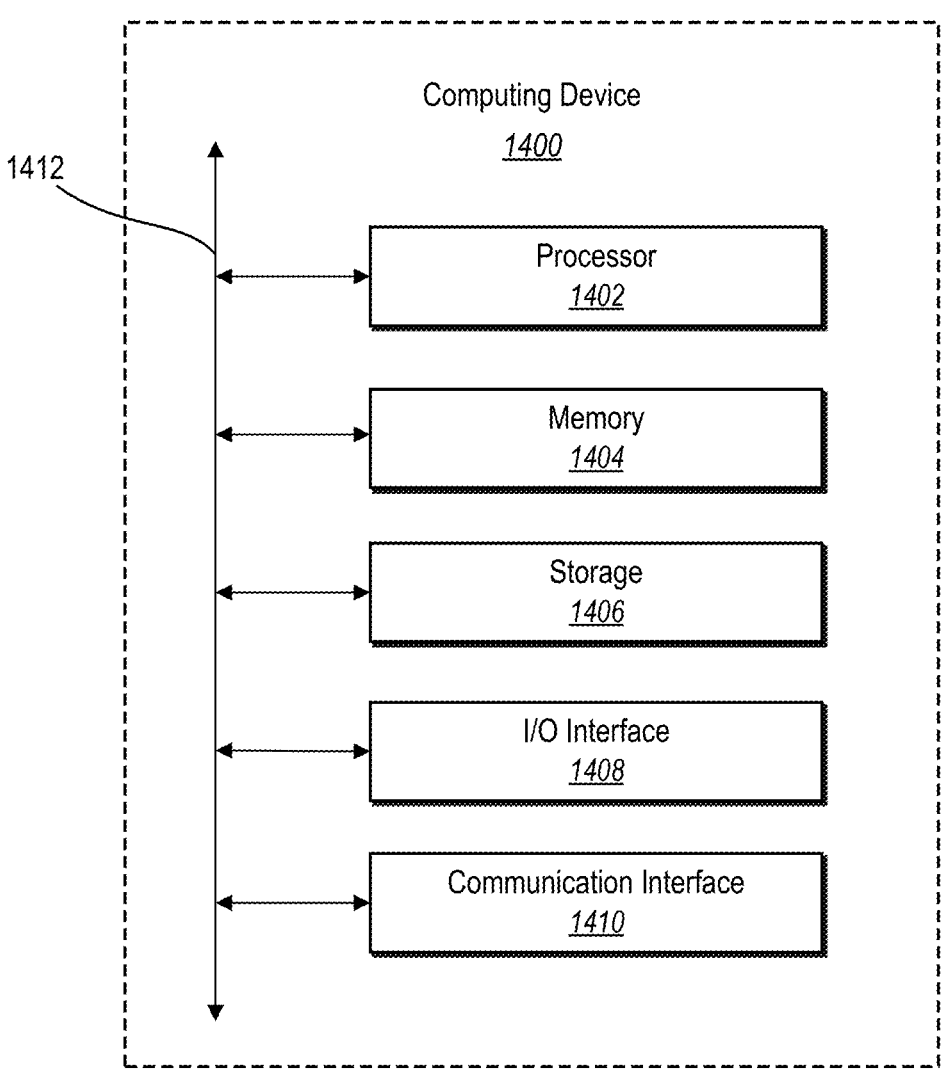
FIG. 14 illustrates a block diagram of an example computing device for implementing one or more embodiments of the present disclosure.

FIG. 14 illustrates a block diagram of exemplary computing device 1400 (e.g., the server(s) 102 and/or the client device(s) 110) that may be configured to perform one or more of the processes described above. One will appreciate that server(s) 102 and/or the client device(s) 110 may comprise one or more computing devices such as computing device 1400. As shown by FIG. 14, computing device 1400 can comprise processor 1402, memory 1404, storage device 1406, I/O interface 1408, and communication interface 1410, which may be communicatively coupled by way of communication infrastructure 1412. While an exemplary computing device 1400 is shown in FIG. 14, the components illustrated in FIG. 14 are not intended to be limiting. Additional or alternative components may be used in other implementations. Furthermore, in certain implementations, computing device 1400 can include fewer components than those shown in FIG. 14. Components of computing device 1400 shown in FIG. 14 will now be described in additional detail.

In particular implementations, processor 1402 includes hardware for executing instructions, such as those making up a computer program. As an example and not by way of limitation, to execute instructions, processor 1402 may retrieve (or fetch) the instructions from an internal register, an internal cache, memory 1404, or storage device 1406 and decode and execute them. In particular implementations, processor 1402 may include one or more internal caches for data, instructions, or addresses. As an example and not by way of limitation, processor 1402 may include one or more instruction caches, one or more data caches, and one or more translation lookaside buffers (TLBs). Instructions in the instruction caches may be copies of instructions in memory 1404 or storage device 1406.

Memory 1404 may be used for storing data, metadata, and programs for execution by the processor(s). Memory 1404 may include one or more of volatile and non-volatile memories, such as Random Access Memory ("RAM"), Read Only Memory ("ROM"), a solid state disk ("SSD"), Flash, Phase Change Memory ("PCM"), or other types of data storage. Memory 1404 may be internal or distributed memory.

Storage device 1406 includes storage for storing data or instructions. As an example and not by way of limitation, storage device 1406 can comprise a non-transitory storage medium described above. Storage device 1406 may include a hard disk drive (HDD), a floppy disk drive, flash memory, an optical disc, a magneto-optical disc, magnetic tape, or a Universal Serial Bus (USB) drive or a combination of two or more of these. Storage device 1406 may include removable or non-removable (or fixed) media, where appropriate. Storage device 1406 may be internal or external to computing device 1400. In particular implementations, storage device 1406 is non-volatile, solid-state memory. In other implementations, Storage device 1406 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

I/O interface 1408 allows a user to provide input to, receive output from, and otherwise transfer data to and receive data from computing device 1400. I/O interface 1408 may include a mouse, a keypad or a keyboard, a touch screen, a camera, an optical scanner, network interface, modem, other known I/O devices or a combination of such I/O interfaces. I/O interface 1408 may include one or more devices for presenting output to a user, including, but not limited to, a graphics engine, a display (e.g., a display screen), one or more output drivers (e.g., display drivers), one or more audio speakers, and one or more audio drivers. In certain implementations, I/O interface 1408 is configured to provide graphical data to a display for presentation to a user. The graphical data may be representative of one or more graphical user interfaces and/or any other graphical content as may serve a particular implementation.

Communication interface 1410 can include hardware, software, or both. In any event, communication interface 1410 can provide one or more interfaces for communication (such as, for example, packet-based communication) between computing device 1400 and one or more other computing devices or networks. As an example and not by way of limitation, communication interface 1410 may include a network interface controller (NIC) or network adapter for communicating with an Ethernet or other wire-based network or a wireless NIC (WNIC) or wireless adapter for communicating with a wireless network, such as a WI-FI.

Additionally or alternatively, communication interface 1410 may facilitate communications with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, communication interface 1410 may facilitate communications with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof.

Additionally, communication interface 1410 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

Communication infrastructure 1412 may include hardware, software, or both that couples components of computing device 1400 to each other. As an example and not by way of limitation, communication infrastructure 1412 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illustrative of the invention and are not to be construed as limiting the invention. Numerous specific details are described to provide a thorough understanding of various embodiments of the present invention.

The present invention may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A computer-implemented method comprising:

receiving a plurality of perturbation images portraying cells from a plurality of wells corresponding to a plurality of cell perturbations;

generating, utilizing a machine learning model, a plurality of well-level image embeddings from the plurality of perturbation images;

aligning, utilizing an alignment model, the plurality of well-level image embeddings to generate aligned well-level image embeddings;

aggregating, according to perturbations of one or more perturbation experiments, the aligned well-level image embeddings to generate perturbation-level image embeddings comprising:

a first perturbation-level image embedding aggregated from a first set of well-level image embeddings having a first shared cell perturbation, and a second perturbation-level image embedding aggregated from a second set of well-level image embeddings having a second shared cell perturbation different from the first shared cell perturbation; and generating perturbation comparisons utilizing the perturbation-level image embeddings.

2. The computer-implemented method of claim 1, wherein receiving the plurality of perturbation images comprises:

receiving a first perturbation image portraying a first cell resulting from at least one of: a first gene knockout perturbation of a first gene or a first compound perturbation; and receiving a second perturbation image portraying a second cell resulting from at least one of: a second gene knockout perturbation of a second gene or a second compound perturbation.

3. The computer-implemented method of claim 2, wherein generating, utilizing the machine learning model, the plurality of well-level image embeddings comprises:

generating, utilizing a convolutional neural network, a first well-level embedding for the first perturbation image; and generating, utilizing the convolutional neural network, a second well-level embedding for the second perturbation image.

4. The computer-implemented method of claim 1, wherein the plurality of perturbation images comprise a plurality of patch images portraying portions of wells from the plurality of wells and wherein generating the plurality of well-level image embeddings comprises:

generating, utilizing the machine learning model, a plurality of patch-level embeddings from the plurality of perturbation images; and aggregating the plurality of patch-level embeddings according to the plurality of wells to generate the plurality of well-level image embeddings.

5. The computer-implemented method of claim 1, further comprising:

receiving an additional plurality of perturbation images portraying additional cells;

generating, utilizing the machine learning model, an additional plurality of well-level image embeddings; and generating modified perturbation-level image embeddings from the additional plurality of well-level image embeddings and the plurality of well-level image embeddings.

6. The computer-implemented method of claim 1, further comprising filtering the plurality of well-level image embeddings according to one or more quality criterion.

7. The computer-implemented method of claim 1, wherein aligning, utilizing the alignment model, the plurality of well-level image embeddings to generate the aligned well-level image embeddings comprises aligning a set of well-level image embeddings from a plurality of different perturbation experiments having a shared perturbation according to a statistical aligning model.

8. The computer-implemented method of claim 1, further comprising:

generating, utilizing a proximity bias model, proximity bias corrected perturbation-level image embeddings; and generating the perturbation comparisons from the proximity bias corrected perturbation-level image embeddings.

9. The computer-implemented method of claim 1, wherein generating the perturbation comparisons utilizing the perturbation-level image embeddings comprises:

determining similarity measures between the perturbation-level image embeddings;

generating a perturbation heatmap comprising the similarity measures for the plurality of cell perturbations; and providing the perturbation heatmap for display via a client device.

10. A system comprising:

at least one processor; and at least one non-transitory computer-readable storage medium storing instructions that, when executed by the at least one processor, cause the system to:

receive a plurality of perturbation images portraying cells from a plurality of wells corresponding to a plurality of cell perturbations;

generate, utilizing a machine learning model, a plurality of well-level image embeddings from the plurality of perturbation images;

align, utilizing an alignment model, the plurality of well-level image embeddings to generate aligned well-level image embeddings;

aggregate, according to perturbations of one or more perturbation experiments, the aligned well-level image embeddings to generate perturbation-level image embeddings comprising:

a first perturbation-level image embedding aggregated from a first set of well-level image embeddings having a first shared cell perturbation, and a second perturbation-level image embedding aggregated from a second set of well-level image embeddings having a second shared cell perturbation different from the first shared cell perturbation; and generate perturbation comparisons utilizing the perturbation-level image embeddings.

11. The system of claim 10, further comprising instructions that, when executed by the at least one processor, cause the system to:

determine statistical significance values for the perturbation-level image embeddings; and filter one or more of the perturbation-level image embeddings having a statistical significance value below a statistical significance threshold.

12. The system of claim 11, wherein the instructions cause the system to generate, utilizing the machine learning model, the plurality of well-level image embeddings by:

generating, utilizing a convolutional neural network, a first well-level embedding for a first perturbation image; and generating, utilizing the convolutional neural network, a second well-level embedding for a second perturbation image.

13. The system of claim 10, wherein the plurality of perturbation images comprise a plurality of patch images portraying portions of wells from the plurality of wells and wherein the instructions cause the system to generate the plurality of well-level image embeddings by:

generating, utilizing the machine learning model, a plurality of patch-level embeddings from the plurality of perturbation images; and aggregating the plurality of patch-level embeddings according to the plurality of wells to generate the plurality of well-level image embeddings.

14. The system of claim 10, further comprising instructions that, when executed by the at least one processor, cause the system to:

receive an additional plurality of perturbation images portraying additional cells;

generate, utilizing the machine learning model, an additional plurality of well-level image embeddings; and generate modified perturbation-level image embeddings from the additional plurality of well-level image embeddings and the plurality of well-level image embeddings.

15. The system of claim 10, wherein the instructions cause the system to align, utilizing the alignment model, the plurality of well-level image embeddings to generate the aligned well-level image embeddings comprises aligning a set of well-level image embeddings from a plurality of different perturbation experiments having a shared perturbation according to a statistical aligning model.

16. A non-transitory computer-readable medium storing instructions that, when executed by at least one processor, cause a computing device to:

receive a plurality of perturbation images portraying cells from a plurality of wells corresponding to a plurality of cell perturbations;

generate, utilizing a machine learning model, a plurality of well-level image embeddings from the plurality of perturbation images;

align, utilizing an alignment model, the plurality of well-level image embeddings to generate aligned well-level image embeddings;

aggregate, according to perturbations of one or more perturbation experiments, the aligned well-level image embeddings to generate perturbation-level image embeddings comprising:

a first perturbation-level image embedding aggregated from a first set of well-level image embeddings having a first shared cell perturbation, and a second perturbation-level image embedding aggregated from a second set of well-level image embeddings having a second shared cell perturbation different from the first shared cell perturbation; and generate perturbation comparisons utilizing the perturbation-level image embeddings.

17. The non-transitory computer-readable medium of claim 16, wherein the instructions cause the computing device to receive the plurality of perturbation images by:

receiving a first perturbation image portraying a first cell resulting from at least one of: a first gene knockout perturbation of a first gene or a first compound perturbation; and receiving a second perturbation image portraying a second cell resulting from at least one of: a second gene knockout perturbation of a second gene or a second compound perturbation.

18. The non-transitory computer-readable medium of claim 17, wherein the instructions cause the computing device to generate, utilizing the machine learning model, the plurality of well-level image embeddings by:

generating, utilizing a convolutional neural network, a first well-level embedding for the first perturbation image; and generating, utilizing the convolutional neural network, a second well-level embedding for the second perturbation image.

19. The non-transitory computer-readable medium of claim 16, wherein the plurality of perturbation images comprise a plurality of patch images portraying portions of wells from the plurality of wells and wherein the instructions cause the computing device to generate the plurality of well-level image embeddings by:

generating, utilizing the machine learning model, a plurality of patch-level embeddings from the plurality of perturbation images; and aggregating the plurality of patch-level embeddings according to the plurality of wells to generate the plurality of well-level image embeddings.

20. The non-transitory computer-readable medium of claim 16, further comprising instructions that, when executed by the at least one processor, cause the computing device to:

receive an additional plurality of perturbation images portraying additional cells;

generate, utilizing the machine learning model, an additional plurality of well-level image embeddings; and generate modified perturbation-level image embeddings from the additional plurality of well-level image embeddings and the plurality of well-level image embeddings.

* * * * *